United States Patent [19]

Millan

[11] Patent Number: 5,707,853

[45] Date of Patent: Jan. 13, 1998

[54] NUCLEIC ACID ENCODING CALF INTESTINAL ALKALINE PHOSPHATASE

[75] Inventor: Jose L. Millan, San Diego, Calif.

[73] Assignee: La Jolla Cancer Research Foundation, La Jolla, Calif.

[21] Appl. No.: 368,071

[22] Filed: Jan. 3, 1995

Related U.S. Application Data

[63] Continuation of Ser. No. 213,371, Mar. 14, 1994, abandoned, which is a continuation of Ser. No. 849,219, Mar. 10, 1992, abandoned.

[51] Int. Cl.⁶ ............................ C12N 15/55; C12N 9/16
[52] U.S. Cl. .................... 435/252.3; 435/325; 435/419; 435/320.1; 435/196; 536/23.2; 536/23.4
[58] Field of Search ........................... 435/196, 320.1, 435/240.1, 240.2, 240.4, 252.3, 325, 419; 536/23.2, 23.4, 24.31

[56] References Cited

U.S. PATENT DOCUMENTS

| | | | |
|---|---|---|---|
| 4,707,438 | 11/1987 | Keydar | 435/5 |
| 5,047,507 | 9/1991 | Buchegger et al. | 530/387 |
| 5,055,415 | 10/1991 | Imai et al. | 436/516 |
| 5,071,761 | 12/1991 | Meyer et al. | 435/243 |
| 5,079,141 | 1/1992 | Niskanen et al. | 435/7.34 |
| 5,079,170 | 1/1992 | Rosman et al. | 436/178 |
| 5,079,171 | 1/1992 | Senyei et al. | 436/510 |
| 5,084,379 | 1/1992 | Calenoff et al. | 435/7.1 |
| 5,089,424 | 2/1992 | Khalil et al. | 436/518 |
| 5,204,244 | 4/1993 | Fell et al. | 435/69.6 |

FOREIGN PATENT DOCUMENTS

| | | |
|---|---|---|
| 159993 | 4/1983 | Germany. |
| 246686 | 6/1987 | Germany. |
| 298424 | 2/1992 | Germany. |

OTHER PUBLICATIONS

Berger et al., "Cloning and Sequencing of Human Intestinal Alkaline Phosphatase cDNA." Proc. Natl. Acad. Sci. USA 84:695–698 (1987).

Besman, M., and Coleman, J.E., "Isozymes of Bovine Intestinal Alkaline Phosphatase," J. Biol. Chem. 260:11190–11193 (1985).

Culp et al., "The Active–Site and Amino–Terminal Amino Acid Sequence of Bovine Intestinal Alkaline Phosphatase." Biochem. Biophys. Acta. 830:330–334 (1985).

Eliakim et al., "Differential Regulation of mRNAs Encoding for Rat Intestinal Alkaline Phosphatase." Am. J. Physiol. 259:G93–98 (1990).

Hahnel et al., "Two Alkaline Phosphatase Genes are Expressed During Early Development in the Mouse Embryo." Development. 110:555–564 (1990).

Henthorn et al., "Sequence and Characterization of the Human Intestinal Alkaline Phosphatase Gene." J. Biol. Chem. 263:12011–12019 (1988).

Hoylaerts, M.F. and Millan, J.L., "Site–directed Mutagenesis and Epitope-mapped Monoclonal Antibodies Define a Catalytically Important Conformational Difference Between Human Placental and Germ Cell Alkaline Phosphatase." Eur. J. Biochem. 202:605–616 (1991).

Knoll et al., "Nucleotide Sequence of the Human Placental Alkaline Phosphatase Gene," J. Biol. Chem. 263:12020–12027 (1988).

Manes et al., "Genomic Structure and Comparison of Mouse Tissue–Specific Alkaline Phosphatase Genes." Genomics. 8:541–554 (1990).

Millan, J.L., and Manes T., "Seminoma–derived Nagao Isozyme is Encoded by a Germ–Cell Alkaline Phosphatase Gene." Proc. Natl. Acad. Sci. USA. 85:3024–3028 (1988).

Millan, J.L., "Promoter Structure of the Human Intestinal Alkaline Phosphatase Gene." Nucl. Acids. Res. 15:10599 (1987).

Millan, J.L., "Oncodevelopmental Expression and Structure of Alkaline Phosphatase Genes." Anticancer Res. 8:995–1004 (1988).

Milstein, C., "The Amino Acid Sequence Around the Reactive Serine Residue in Alkaline Phosphatase from *Escherichia coli*." Biochem. J. 92:410–422 (1964).

Tsonis, et al., "A Putative Functional Domain of Human Placental Alkaline Phosphatase Predicted from Sequence Comparisons." Biochem. J. 254:623–624 (1988).

Weissig et al., "Cloning and Expression of the Bovine Intestinal Alkaline Phosphatase Gene Biochemical Characterization of the Recominant Enzyme," Biochem. J. 290(2):503–508 (1993).

Culp et al., "Expression of Bovine Intestinal Alkaline Phosphatase in *Escherichia–coli*," *69th Annual Meeting of the Federation of American Societies for Experimental Biology* Anaheim, CA (1985).

Sambrook et al., *Molecular Cloning: A Laboratory Manual*, 1989, pp. 11.3–11.19.

Millan, J. Prog. Clin. Biol. Res. 344:453–475, 1990.

*Primary Examiner*—Keith D. Hendricks
*Attorney, Agent, or Firm*—Campbell & Flores LLP

[57] ABSTRACT

The invention relates to isolated nucleic acids encoding recombinant calf intestinal alkaline phosphatase. Expression vectors and host cells transformed or transfected with such vectors are also provided. The invention further provides multifunctional polypeptides containing amino acid sequences encoding for calf intestinal alkaline phosphatase and a second amino acid sequence encoding a reagent having specific reactivity with a ligand. The recombinant calf intestinal alkaline phosphatase or its active fragments and the multifunctional polypeptides can be used in the methods for determining the presence or concentration of a ligand.

9 Claims, 7 Drawing Sheets

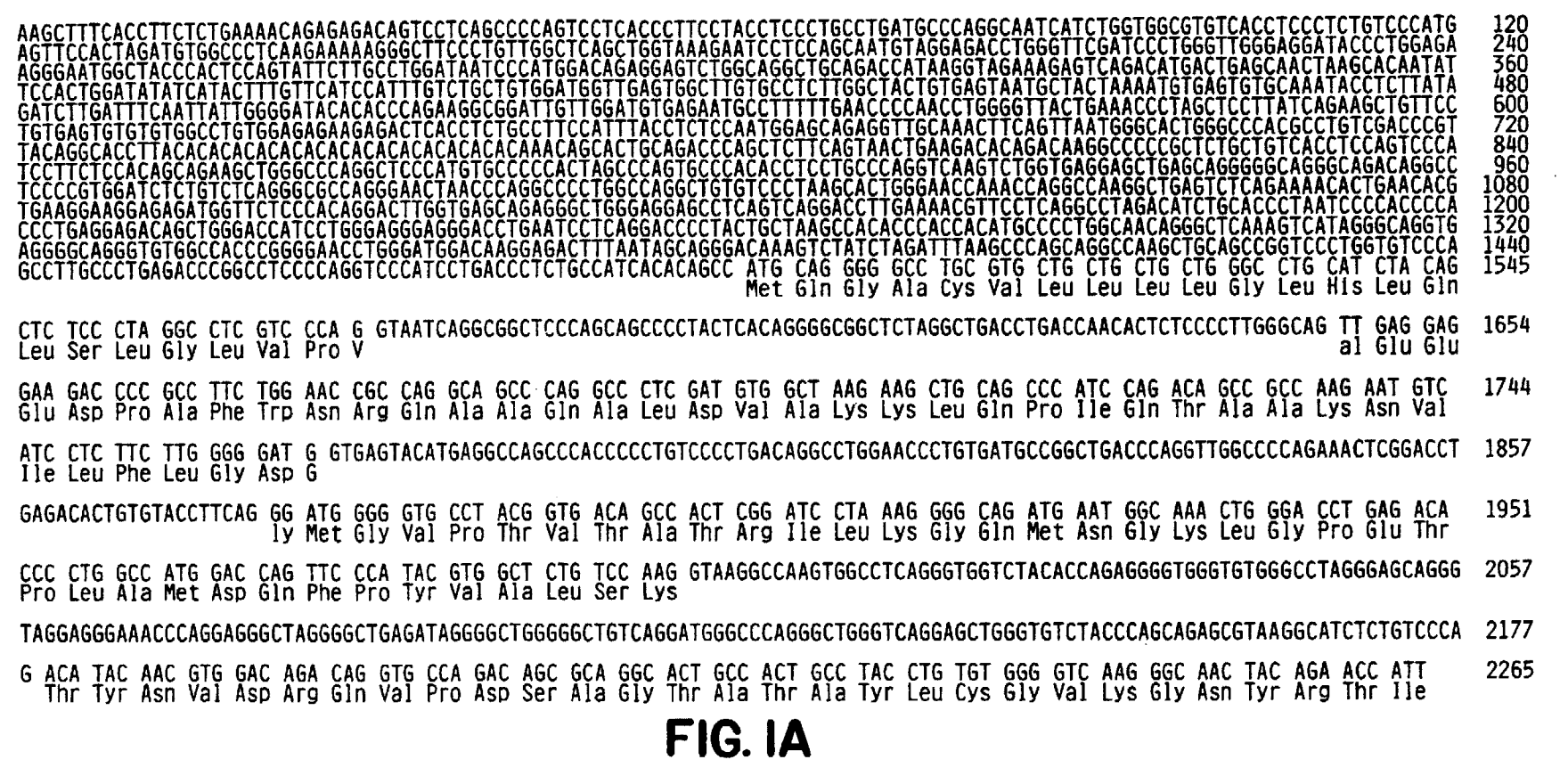

FIG. IA

```
GGT GTA ATG GCA GCC CGC TAC AAC CAG TGC AAA ACG ACA CGT GGG AAT GAG GTC ACG TCT GTG ATG AAC CGG GCC AAG AAA GCA GT    2355
Gly Val Met Ala Ala Arg Tyr Asn Gln Cys Lys Thr Thr Arg Gly Asn Glu Val Thr Ser Val Met Asn Arg Ala Lys Lys Ala G

GGGCTTGGGCGTCAGCTTCCTGGGCAGGGACGGGCTCAGAGACCTCAGTGGCCCAGTGGCCCACCGTGACCTCTGCCACCCTCAG GG AAG TCC GTG GGA GTG GTG ACC AGG    2464
                                                                                    ly Lys Ser Val Gly Val Val Thr Arg

GTG CAG CAT GCC TCC CCA GCC CAC GGG GCC TAC GCC CAC ACG GTG AAC CGA AAC TGG TAC TCA GAC GCC GAC CTG CCT GCT GAT GCA ATG    2554
Val Gln His Ala Ser Pro Ala His Gly Ala Tyr Ala His Thr Val Asn Arg Asn Trp Tyr Ser Asp Ala Asp Leu Pro Ala Asp Ala Met

AAT GGC TGC CAG GAC ATC GCC GCA GCA ATC GTC AAC CTG GTC AAC ATG AAT GAT ATT GAC GTGCGACATGTTGGGCACAGGGCGGGGCTGGGCACAGCTGGTGGGGCACACT    2657
Asn Gly Cys Gln Asp Ile Ala Ala Ala Ile Val Asn Leu Val Asn Met Asn Asp Ile Asp

CGCAACACAGTCGTAGGTAACCTCCAGCCTGCGGTGTTTCAGGGTTTTGTGTGTGTGGGGTGGCACCATGTAGGAGGTGGCCACAGGGCCTTTCCCACA    2777

GACCTGGTGGGGCAGGTAGGGCTGTGTGAGAGGAGTAAAGGGCCAGGCCCTAACCACCTCTGGCTCCAG GTG ATC CTG GGT GCA GGC CGA AAA CTG GTG CAG    2887
                                                                    Val Ile Leu Gly Val Gly Gly Arg Lys Leu Val Gln

TAC ATG TTT CCT GTG GGG ACC CCA GAC CCT GAA TAC CCA GAT GAT GCA AGT GTG AAT GGA GTC CGG AAG CAG AAC CTG AAT GTC TAC CAG    2977
Tyr Met Phe Pro Val Gly Thr Pro Asp Pro Glu Tyr Pro Asp Asp Ala Ser Val Asn Gly Val Arg Lys Gln Asn Leu Val Gln

GAT GCC ATG GGG CTC ACG GGG TAATGGGGCTCACGGGGTACAGTGGGGCTGGGCCTATGGCTGCGAGGCCTGGTTCTGCCCTCCCAG GGA    3086
Asp Ala Met Gly Leu Thr Gly                                                                          Gly

GCA TGG CAG CAC CAG AAG GCC TAT GTG AAC CGC ACT GCG CTC CTT CAG GCC CCC GAT GAC TCC AGT GTA ACA CAC CTC ATG G    3182
Ala Trp Gln His Gln Lys Ala Tyr Val Asn Arg Thr Ala Leu Leu Gln Ala Pro Asp Asp Ser Ser Val Thr His Leu Met G

GCC CAG TAT GTG GTG TGG AAC CGC ACT GCG CTC CTT CAG GCC CCC GAT GAC TCC AGT GTA ACA CAC CTC ATG G GTAACGACTCCACCCACCCCCACTGT    3182
Ala Gln Tyr Val Val Trp Asn Arg Thr Ala Leu Leu Gln Ala Pro Asp Asp Ser Ser Val Thr His Leu Met G

CCTCCCCAGGAATGGGTGCCATGGGGCCACCCCTGTCCTCAGCTTGACGGTCACCACTGCTCCCCTTTCCCACAG GC CTC TTT GAG CCG GCA GAC ATG AAG TAT AAT    3288
                                                                                Ly Leu Phe Glu Pro Ala Asp Met Lys Tyr Asn

GTT CAG CAA GAC CAC ACC CTG CAG GAA ATG ACA GAG CCG GTA AGC GTC CGA GTG GCC CTG AAG GTG AGC AGG AAC CCC AGG GGC TTC TAC    3378
Val Gln Gln Asp His Thr Leu Gln Glu Met Thr Glu Pro Val Ser Val Arg Val Ala Leu Lys Val Ser Arg Asn Pro Arg Gly Phe Tyr

CTC TTT GTG GAG G GTGAGTGGCAGCCCCTTGGTGAACAGAGAGGTGTGATGAGGGCCATCAGGGTGGGTTTGGTATCTTATATGTGACTTATCTGCAG GA GGC CGC ATT GAC    3488
Leu Phe Val Glu G                                                                                                ly Gly Arg Ile Asp
```

FIG. 1B

```
CAC GGT CAC CAT GAT GAC AAA GCT TAT ATG GCA CTG ACC GAG GCG GGT ATG TTT GAC AAT GCC ATC GCC AAG GCT AAT GAG CTC ACT AGC   3578
His Gly His His Asp Asp Lys Ala Tyr Met Ala Leu Thr Glu Ala Gly Met Phe Asp Asn Ala Ile Ala Lys Ala Asn Glu Leu Thr Ser

GAA CTG GAC ACG ATC CTT GTC ACT GCA GAC CAC TCT CAT GTC TTC TTT GGT GGC TAT GGC ACA CTG CGT GGG ACC TCC ATT TTT G GT       3668
Glu Leu Asp Thr Ile Leu Val Thr Ala Asp His Ser His Val Phe Phe Gly Gly Tyr Gly Thr Leu Arg Gly Thr Ser Ile Phe G

AAGCCCAGGAGAGTGGCAGGTCGTTGCCCTAAGTTACGAGGGCACACAGGGAGCACAGAGTTCCTCTATCGTCTAGTGGGTAGTACAGACACTGCTGCTACGCTCTGGTGAGGA         3788

TTGTCACTGACAGACTGGCCATGGCTCTGCACACAGGGAGCTAGTGCAGTGTGATCACGGGGTCCCCTCTTCCCTGAAG GT CTG GCC CCC AGC AAG GCC              3898
                                                                                 ly Leu Ala Pro Ser Lys Ala

TTA GAC AGC AAG TCC TAC ACC ATC CTC TAT GGC AAT GGC CCA GGC TAT GCG CTT GGC GGG TCG AGG CCC GAT GTT AAT GAC AGC           3988
Leu Asp Ser Lys Ser Tyr Thr Ile Leu Tyr Gly Asn Gly Pro Gly Tyr Ala Leu Gly Gly Ser Arg Pro Asp Val Asn Asp Ser

ACA AGC G GTAAGTGTAGTAGGTGGGGCGCTGGAGGTGGGACCCTGGCCAGAAATTGTGGGAGGGAAGGCTGCCTCCCTGTCACATTAACTTCCCTTTTTCTGGCCAG AG         4102
Thr Ser G                                                                                                       lu

GAC CCC TCG TAC CAG CAG GCG GCC GTG CCC CAG AGC GAG GAG ACC CAC GGG GGC GTG TTC GCG GGC CGC CGG CAG                      4192
Asp Pro Ser Tyr Gln Gln Ala Ala Val Pro Gln Ser Glu Glu Thr His Gly Gly Val Phe Ala Arg Gly Pro Gln

GCG CAC CTG GTC GTG GGC GTG GAG GAG ATC CAC GCG TTC GCC CAC ATC ATG GCC TTC GTG GGC TGC GAG CCC TAC ACC GAC TGC AAT        4282
Ala His Leu Val Val Gly Val Glu Glu Ile His Ala Phe Ala His Ile Met Ala Phe Val Gly Cys Val Glu Pro Tyr Thr Asp Cys Asn

CTG CCA GCC ACC ACC GCA CTG CTG GCC AGC CCG CCT CCA CTG GCG CTG GCT GGG GCG ATG                                          4372
Leu Pro Ala Thr Thr Ala Ser Pro Pro Pro Leu Ala Leu Ala Gly Ala Met

CTG CTG CTG GCG CCC ACC TTG TAC TAA CCCCACCAGTTCCAGGTCTCCAGGATTCCCGCTCTCCTGCCAAAACCTCCCAGTCAGGCCCTACCGGAGCTACCACC        4482
Leu Leu Leu Ala Pro Thr Leu Tyr ***

TCAGAGTCCCACCCCGAAGTGTATCCTAGTCTGCCACTCCTGCAGACCCGGCCCCACCGGCCCGACCGGAGTTTCACCTCCCAGCAGTGATTCACATTGAAGGAGCCTCAGC        4602
TAACAGCCCTTCAAGGGCCTATACGGAGGCTCTGATTTCCTTGACACGCTGAGACTACTGCCCTGTGACACTGGACGCTAGACAAAGACCTAGCTGCCTGGCTTGCTGTCTGCACCCT 4722
GAACCTCAGTAAGGGGCTCGGGTTCGGAGAGTGGCTTCGGAGGCGTGGTTTCCGATCCAGATGGCTGCCCTGAACGTGCCCTGGAACCAACCTGTGCTACACCTGGCCACCAG      4842
AGCGGACTGGACTCTGGGCCTGGGTTTCCAGAAGTGGACGTTGGGCCTAGAACAGAACAGGAGACAGCAGGGCATCCAGTAGCAGCCCGCGCCCTCCCTGGAGGCAGGAAGCAGG    4962
GCCCTCGGACCTGGAACCTTGGGACACTCGAAGAGCCCTTCCTCCAGAGAACGCAAGTGTCCCAGGGTAGCAGCAGCAGGCACAGAGTCTCTGGGTGAGGGGGCACAGCCCTTAGG 5082
GCCCTGGGACCTGGGACTCCCCTTCAAGAGTGTGATACATGTGAAGAGAAGAACCTCAGTCAGGGGCACAGTGTGGTGTCAGGGTGTGGTGGGGACTGGTGCAGGAGGTTAGGGAGG 5202
GATACAGGAGTGAACCAAGGACCAACTCAGAGAGGGCAACTCAGAGACATCAGGAGGGTCACATCAGGGTCAGGGGACTGGGACTGGTGCAGGAGGTTAGGGAGGGT           5322
GCAAAGACCAAGGACCAACTCAGAGGCAACTGGTGCAGGGCACTGGTGTGGTCGTTGA                                                              5399
```

```
A A Q A L D V A K K L Q P I Q T A A K N V I L F L G D    42   b.IAP
- K E - - - - - - - - - - - - - S - - - L - - - - - -   42   r.IAP
- - E - - - A - - - - - - - - - S - - - L - I - - - -   42   m.IAP
- - E - - - A - - - - - - - - K V - - - L - - - - - -   42   h.IAP

A L S K T Y H V D R Q V P D S A G T A T A Y L C G V K   104   b.IAP
- - - - - - - - - - - - - - - - - - - - - - - - - - -   104   r.IAP
- - - - - S - - - - - - - - - - S - - - - - - - - - -   104   m.IAP
- - - - - - - - - - - - - - - A - - - - - - - - - - -   104   h.IAP

G K S V G V V T T T R V Q H A S P A G A Y A H T V H R   166   b.IAP
- - - - - - - - - - - - - - - - - - - T - - - - - - -   166   r.IAP
- - - - - - - - - - - - - - - S - T - V - - - - - - -   166   m.IAP
- - - - - - - - - - - - - - - - - T - - - - - - - - -   166   h.IAP

G G R K Y M F P V G T P D P E Y P D D A S V N G V R K   228   b.IAP
- - - - - F - - - K - - - - - - - G - S D Q S - - - L   228   r.IAP
- - - - - - - - - A M - - - - - - H - - N E T - T - L   228   m.IAP
- - - - - - - - - M - - - - - - - A - - - Q - - I - L   228   h.IAP

H L M G L F E P A D M K Y H V Q Q D H T K D P T L Q E   290   b.IAP
R Y - - - - - - T E - - - D - H R N A S A - - S - A -   290   r.IAP
Y - - - - - - - V - T - F D I - R - P L M - - S - K D   290   m.IAP
- - - - - - - G - T - - E I H R - P - L - - - S - M -   290   h.IAP

M A L T E A G M F D H A I A K A H E L T S E L D T L I   352   b.IAP
L - - - - - V - - - S - - E - - S Q - - H - K - - - T   352   r.IAP
L - - - - - V - - - L - - E R - S Q - - - - R - - - T   352   m.IAP
Q - - - - - V - - - D - - E R - G Q - - - E - - - - T   352   h.IAP

Y T S I L Y G N G P G Y A L G G G S R P D V H D S T S   414   b.IAP
- - - - - - - - - - - - - V - N S - H - - N - T - A E -   414   r.IAP
- - - - - - - - - - - - - V G - T - E - - N - T A A E -   413   m.IAP
- - - T - - - - - - - - - V F H S - V - - - - E S E -   414   h.IAP

H G V E E E T F V A H I M A F A G C V E P Y T D C H L   476   b.IAP
- - - Q - Q H Y I - - V - - - - - L - - - - - - - G -   476   r.IAP
- - - Q - Q H Y I - - V - - S - - - L - - - - - - G -   475   m.IAP
- - - Q - Q S - - - - V - - - A - L - - - - - A - D -   476   h.IAP

T L Y                                                    514   b.IAP
L V G T A L V V S                                        520   r.IAP
A R S L G P A T A P L A L A L L A G M L M L L L G A P A E   540   m.IAP
                                                         508   h.IAP
```

FIG. 3B

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:1:

Met  Lys  Asn  His  Glu
  1                        5

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCTAGCCATG CAGGGGGCCT GCG                    23

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCGGCCGCCT GAAGGAGC                                    18

( 2 ) INFORMATION FOR SEQ ID NO:4:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: complement (1)
        ( D ) OTHER INFORMATION: /note= "N=C OR A"

( i x ) FEATURE:
        ( A ) NAME/KEY: misc_feature
        ( B ) LOCATION: complement (2)
        ( D ) OTHER INFORMATION: /note= "N=AG OR GT"

( i x ) FEATURE:
        ( A ) NAME/KEY: misc_feature
        ( B ) LOCATION: complement (3)
        ( D ) OTHER INFORMATION: /note= "N=A OR G"

( x i ) SEQUENCE DESCRIPTION: SEQ ID NO:4:

NNNAGT                                                      6

( 2 ) INFORMATION FOR SEQ ID NO:5:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: complement (1)
        ( D ) OTHER INFORMATION: /note= "Y=T OR C"

( i x ) FEATURE:
        ( A ) NAME/KEY: misc_feature
        ( B ) LOCATION: complement (3)
        ( D ) OTHER INFORMATION: /note= "Y=C OR T"

( i x ) FEATURE:
        ( A ) NAME/KEY: misc_feature
        ( B ) LOCATION: complement (4)
        ( D ) OTHER INFORMATION: /note= "Y=AG OR G"

( x i ) SEQUENCE DESCRIPTION: SEQ ID NO:5:

YNYY                                                            4

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CACACCTCCT GCCCAGNNNN NNNCTGGTGA GGAGCTGAG            39

( 2 ) INFORMATION FOR SEQ ID NO:7:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:7:

AGCCACACCC                                                                                     10

( 2 ) INFORMATION FOR SEQ ID NO:8:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:8:

ACAGAGAGGA GA                                                                                  12

( 2 ) INFORMATION FOR SEQ ID NO:9:

( i ) SEQUENCE CHARACTERISTICS:
      ( A ) LENGTH: 5399 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: join(1501..1567, 1647..1763, 1878..1993, 2179
         . . 2353, 2433..2605, 2864..2998, 3084..3156, 3257
         . . 3391, 3475..3666, 3879..3995, 4101..4402)

( x i ) SEQUENCE DESCRIPTION: SEQ ID NO:9:

| AAGCTTTCAC | CTTCTCTGAA | AACAGAGAGA | CAGTCCTCAG | CCCCAGTCCT | CACCCTTCCT | 60 |
| AGCTCCCTGC | CTGATGCCCA | GGCAATCATC | TGGTGGCGTG | TCACCTCCCT | CTGTCCATG | 120 |
| AGTTCCACTA | GATGTGGCCC | TCAAGAAAAA | GGGCTTCCCT | GTTGGCTCAG | CTGGTAAAGA | 180 |
| ATCCTCCAGC | AATGTAGGAG | ACCTGGGTTC | GATCCCTGGG | TTGGGAGGAT | ACCCTGGAGA | 240 |
| AGGGAATGGC | TACCCACTCC | AGTATTCTTG | CCTGGATAAT | CCCATGGACA | GAGGAGTCTG | 300 |
| GCAGGCTGCA | GACCATAAGG | TAGAAGAGT | CAGACATGAC | TGAGCAACTA | AGCACAATAT | 360 |
| TCCACTGGAT | ATATCATACT | TTGTTCATCC | ATTTGTCTGC | TGTGGATGGT | TGAGTGGCTT | 420 |
| GTGCCTCTTG | GCTACTGTGA | GTAATGCTAC | TAAAATGTGA | GTGTGCAAAT | ACCTCTTATA | 480 |
| GATCTTGATT | TCAATTATTG | GGGATACACA | CCCAGAAGGC | GGATTGTTGG | ATGTGAGAAT | 540 |
| GCCTTTTTGA | ACCCCAACCT | GGGGTTACTG | AAACCCTAGC | TCCTTATCAG | AAGCTGTTCC | 600 |
| TGTGAGTGTG | TGTGGCCTGT | GGAGAGAAGA | GACTCACCTC | TGCCTTCCAT | TTACCTCTCC | 660 |
| AATGGAGCAG | AGGTTGCAAA | CTTCAGTTAA | TGGGCACTGG | GCCCACGCCT | GTCGACCCGT | 720 |
| TACAGGCACC | TTACACACAC | ACACACACAC | ACACACACAC | ACAAACAGCA | CTGCAGACCC | 780 |
| AGCTCTTCAG | TAACTGAAGA | CACAGACAAG | GCCCCGCTC | TGCTGTCACC | TCCAGTCCCA | 840 |
| TCCTTCTCCA | CAGCAGAAGC | TGGGCCCAGG | CTCCCATGTG | CCCCCACTAG | CCCAGTGCCC | 900 |
| ACACCTCCTG | CCCAGGTCAA | GTCTGGTGAG | GAGCTGAGCA | GGGGCAGGG | CAGACAGGCC | 960 |
| TCCCCGTGGA | TCTCTGTCTC | AGGGCGCCAG | GGAACTAACC | CAGGCCCCTG | GCCAGGCTGT | 1020 |

```
GTCCCTAAGC ACTGGGAACC AAACCAGGCC AAGGCTGAGT CTCAGAAAAC ACTGAACACG      1080

TGAAGGAAGG AGAGATGGTT CTCCCACAGG ACTTGGTGAG CAGAGGGCTG GGAGGAGCCT      1140

CAGTCAGGAC CTTGAAAACG TTCCTCAGGC CTAGACATCT GCACCCTAAT CCCCACCCCA      1200

CCCTGAGGAG ACAGCTGGGA CCATCCTGGG AGGGAGGGAC CTGAATCCTC AGGACCCCTA      1260

CTGCTAAGCC ACACCCACCA CATGCCCCTG GCAACAGGGC TCAAAGTCAT AGGGCAGGTG      1320

AGGGGCAGGG TGTGGCCACC CGGGGAACCT GGGATGGACA AGGAGACTTT AATAGCAGGG      1380

ACAAAGTCTA TCTAGATTTA AGCCCAGCAG GCCAAGCTGC AGCCGGTCCC TGGTGTCCCA      1440

GCCTTGCCCT GAGACCCGGC CTCCCCAGGT CCCATCCTGA CCCTCTGCCA TCACACAGCC      1500

ATG CAG GGG GCC TGC GTG CTG CTG CTG CTG GGC CTG CAT CTA CAG CTC       1548
Met Gln Gly Ala Cys Val Leu Leu Leu Leu Gly Leu His Leu Gln Leu
 1               5                  10                  15

TCC CTA GGC CTC GTC CCA  G GTAATCAGGC GGCTCCCAGC AGCCCCTACT           1597
Ser Leu Gly Leu Val Pro
              20

CACAGGGGCG GCTCTAGGCT GACCTGACCA ACACTCTCCC CTTGGGCAG TT GAG          1651
                                                        Val Glu

GAG GAA GAC CCC GCC TTC TGG AAC CGC CAG GCA GCC CAG GCC CTC GAT      1699
Glu Glu Asp Pro Ala Phe Trp Asn Arg Gln Ala Ala Gln Ala Leu Asp
 25              30                  35                  40

GTG GCT AAG AAG CTG CAG CCC ATC CAG ACA GCC GCC AAG AAT GTC ATC      1747
Val Ala Lys Lys Leu Gln Pro Ile Gln Thr Ala Ala Lys Asn Val Ile
             45                  50                  55

CTC TTC TTG GGG GAT  G GTGAGTACAT GAGGCCAGCC CACCCCCTGT              1793
Leu Phe Leu Gly Asp
             60

CCCCTGACAG GCCTGGAACC CTGTGATGCC GGCTGACCCA GGTTGGCCCC AGAAACTCGG    1853

ACCTGAGACA CTGTGTACCT TCAG GG ATG GGG GTG CCT ACG GTG ACA GCC        1903
                         Gly Met Gly Val Pro Thr Val Thr Ala
                                  65                  70

ACT CGG ATC CTA AAG GGG CAG ATG AAT GGC AAA CTG GGA CCT GAG ACA      1951
Thr Arg Ile Leu Lys Gly Gln Met Asn Gly Lys Leu Gly Pro Glu Thr
             75                  80                  85

CCC CTG GCC ATG GAC CAG TTC CCA TAC GTG GCT CTG TCC AAG              1993
Pro Leu Ala Met Asp Gln Phe Pro Tyr Val Ala Leu Ser Lys
         90                  95                 100

GTAAGGCCAA GTGGCCTCAG GGTGGTCTAC ACCAGAGGGG TGGGTGTGGG CCTAGGGAGC    2053

AGGGTAGGAG GGAAACCCAG GAGGGCTAGG GGCTGAGATA GGGGCTGGGG GCTGTGAGGA    2113

TGGGCCCAGG GCTGGGTCAG GAGCTGGGTG TCTACCCAGC AGAGCGTAAG GCATCTCTGT    2173

CCCAG ACA TAC AAC GTG GAC AGA CAG GTG CCA GAC AGC GCA GGC ACT        2220
      Thr Tyr Asn Val Asp Arg Gln Val Pro Asp Ser Ala Gly Thr
                   105                 110

GCC ACT GCC TAC CTG TGT GGG GTC AAG GGC AAC TAC AGA ACC ATT GGT      2268
Ala Thr Ala Tyr Leu Cys Gly Val Lys Gly Asn Tyr Arg Thr Ile Gly
115                 120                 125                 130

GTA AGT GCA GCC GCC CGC TAC AAC CAG TGC AAA ACG ACA CGT GGG AAT      2316
Val Ser Ala Ala Ala Arg Tyr Asn Gln Cys Lys Thr Thr Arg Gly Asn
            135                 140                 145

GAG GTC ACG TCT GTG ATG AAC CGG GCC AAG AAA GCA G GTGGGCTTGG         2363
Glu Val Thr Ser Val Met Asn Arg Ala Lys Lys Ala
            150                 155

GCGTCAGCTT CCTGGGCAGG GACGGGCTCA GAGACCTCAG TGGCCCACCG TGACCTCTGC    2423

CACCCTCAG GG AAG TCC GTG GGA GTG GTG ACC ACC ACC AGG GTG CAG         2470
           Gly Lys Ser Val Gly Val Val Thr Thr Thr Arg Val Gln
               160                 165                 170
```

```
CAT GCC TCC CCA GCC GGG GCC TAC GCG CAC ACG GTG AAC CGA AAC TGG        2518
His Ala Ser Pro Ala Gly Ala Tyr Ala His Thr Val Asn Arg Asn Trp
            175             180                 185

TAC TCA GAC GCC GAC CTG CCT GCT GAT GCA CAG ATG AAT GGC TGC CAG        2566
Tyr Ser Asp Ala Asp Leu Pro Ala Asp Ala Gln Met Asn Gly Cys Gln
            190             195                 200

GAC ATC GCC GCA CAG CTG GTC AAC AAC ATG GAT ATT GAC GTGCGACATG         2615
Asp Ile Ala Ala Gln Leu Val Asn Asn Met Asp Ile Asp
            205             210             215

TTGGGCACAG GGCGGGGCTG GGCACAGGTG GTGGGGCACA CTCGCAACAC AGTCGTAGGT      2675
AACCTCCAGC CTGCGGTGTT TCAGGGTTTT CATGGGTTTG TGTGTGTGTG TATGTGTGGT      2735
GGGGTGGCAC CATGTAGGAG GTGGGGACAG GCCTTTCCCA CAGACCTGGT GGGGGAGGTA      2795
GGGGCTGTGT GAGAGGAGTA AAGGGCCAGC CAGGCCCCTA ACCCACCTGC CTAACTCTCT      2855

GGCTCCAG GTG ATC CTG GGT GGA GGC CGA AAA TAC ATG TTT CCT GTG GGG      2905
         Val Ile Leu Gly Gly Gly Arg Lys Tyr Met Phe Pro Val Gly
                 220             225                 230

ACC CCA GAC CCT GAA TAC CCA GAT GAT GCC AGT GTG AAT GGA GTC CGG       2953
Thr Pro Asp Pro Glu Tyr Pro Asp Asp Ala Ser Val Asn Gly Val Arg
            235             240                 245

AAG CGA AAG CAG AAC CTG GTG CAG GCA TGG CAG GCC AAG CAC CAG           2998
Lys Arg Lys Gln Asn Leu Val Gln Ala Trp Gln Ala Lys His Gln
            250             255             260

GTAATGGGGG CTCACGGATG TGGGGGTACA GTGGGCTGG GCCTGGGGTG TCGGCTATGG       3058
CTGAGGCCTG GTTCTGCCCT CCAG GGA GCC CAG TAT GTG TGG AAC CGC ACT        3110
                           Gly Ala Gln Tyr Val Trp Asn Arg Thr
                                   265             270

GCG CTC CTT CAG GCG GCC GAT GAC TCC AGT GTA ACA CAC CTC ATG G         3156
Ala Leu Leu Gln Ala Ala Asp Asp Ser Ser Val Thr His Leu Met
            275             280                 285

GTAACGACTC CACCCACCCT CACTGTCCTC CCCAGGAATG GGTGCCATGG GCCACCCCTG      3216
TCCTCAGCTT GAGGGTCACC ACTGCTCCCC TTTCCCACAG GC CTC TTT GAG CCG        3270
                                              Gly Leu Phe Glu Pro
                                                              290

GCA GAC ATG AAG TAT AAT GTT CAG CAA GAC CAC ACC AAG GAC CCG ACC       3318
Ala Asp Met Lys Tyr Asn Val Gln Gln Asp His Thr Lys Asp Pro Thr
            295             300                 305

CTG CAG GAA ATG ACA GAG GTG GCC CTG CGA GTC GTA AGC AGG AAC CCC       3366
Leu Gln Glu Met Thr Glu Val Ala Leu Arg Val Val Ser Arg Asn Pro
            310             315                 320

AGG GGC TTC TAC CTC TTT GTG GAG G GTGAGTGGCA GCCCCTTGGT               3411
Arg Gly Phe Tyr Leu Phe Val Glu
            325             330

GAACAGAGGT GTGATGAGGG CCATCAGGGT GGGTTTGGTA TCTTATATGT GACTTATCTG      3471
CAG GA GGC CGC ATT GAC CAC GGT CAC CAT GAT GAC AAA GCT TAT ATG        3518
    Gly Gly Arg Ile Asp His Gly His His Asp Asp Lys Ala Tyr Met
                     335             340                 345

GCA CTG ACC GAG GCG GGT ATG TTT GAC AAT GCC ATC GCC AAG GCT AAT       3566
Ala Leu Thr Glu Ala Gly Met Phe Asp Asn Ala Ile Ala Lys Ala Asn
            350             355                 360

GAG CTC ACT AGC GAA CTG GAC ACG CTG ATC CTT GTC ACT GCA GAC CAC       3614
Glu Leu Thr Ser Glu Leu Asp Thr Leu Ile Leu Val Thr Ala Asp His
            365             370                 375

TCT CAT GTC TTC TCT TTT GGT GGC TAT ACA CTG CGT GGG ACC TCC ATT       3662
Ser His Val Phe Ser Phe Gly Gly Tyr Thr Leu Arg Gly Thr Ser Ile
            380             385                 390
```

```
TTT   G GTAAGCCCAG GGAGAGTGGC AGGTCGTTGC CCCTAAGTTA CGAGGCACAA          3716
Phe

CTCGTCTGAG CCAGTTCCTC TATCTGTCTA GTGGGGTAGT ACAGCACACT GCCTGCTACG       3776

CTCTGGTGAG GATTGTCACT GACAGACAGA CTGGCCATGG CTCTGCACAC AGGGGAGCAC       3836

AAGCTAGGTC AGTGTGATCA CGGGGTCCCC TCTTCCCTGA AG   GT CTG GCC CCC        3889
                                                    Gly Leu Ala Pro
                                                        395

AGC AAG GCC TTA GAC AGC AAG TCC TAC ACC TCC ATC CTC TAT GGC AAT        3937
Ser Lys Ala Leu Asp Ser Lys Ser Tyr Thr Ser Ile Leu Tyr Gly Asn
        400                 405                 410

GGC CCA GGC TAT GCG CTT GGC GGG GGC TCG AGG CCC GAT GTT AAT GAC        3985
Gly Pro Gly Tyr Ala Leu Gly Gly Gly Ser Arg Pro Asp Val Asn Asp
415                 420                 425                 430

AGC ACA AGC  G GTAAGTGTAG TAGGTGGGGC GCTGGGAGGT GGGGACCCTG              4035
Ser Thr Ser

GCCAGAAATT GTGGGGAGGG GAAGGCTGCC TCCCTTGTCA CATTAACTTC CCTTCTTCTG       4095

GCCAG  AG GAC CCC TCG TAC CAG CAG CAG GCG GCC GTG CCC CAG GCT          4141
       Glu Asp Pro Ser Tyr Gln Gln Gln Ala Ala Val Pro Gln Ala
                435                 440                 445

AGC GAG ACC CAC GGG GGC GAG GAC GTG GCG GTG TTC GCG CGC GGC CCG        4189
Ser Glu Thr His Gly Gly Glu Asp Val Ala Val Phe Ala Arg Gly Pro
        450                 455                 460

CAG GCG CAC CTG GTG CAC GGC GTC GAG GAG GAG ACC TTC GTG GCG CAC        4237
Gln Ala His Leu Val His Gly Val Glu Glu Glu Thr Phe Val Ala His
465             470                 475

ATC ATG GCC TTT GCG GGC TGC GTG GAG CCC TAC ACC GAC TGC AAT CTG        4285
Ile Met Ala Phe Ala Gly Cys Val Glu Pro Tyr Thr Asp Cys Asn Leu
480             485                 490                 495

CCA GCC CCC ACC ACC GCC ACC AGC ATC CCC GAC GCC GCG CAC CTG GCG        4333
Pro Ala Pro Thr Thr Ala Thr Ser Ile Pro Asp Ala Ala His Leu Ala
                500                 505                 510

GCC AGC CCG CCT CCA CTG GCG CTG CTG GCT GGG GCG ATG CTG CTG CTG        4381
Ala Ser Pro Pro Pro Leu Ala Leu Leu Ala Gly Ala Met Leu Leu Leu
        515                 520                 525

CTG GCG CCC ACC TTG TAC TAACCCCCAC CAGTTCCAGG TCTCGGGATT               4429
Leu Ala Pro Thr Leu Tyr
        530

TCCCGCTCTC CTGCCCAAAA CCTCCCAGCT CAGGCCCTAC CGGAGCTACC ACCTCAGAGT       4489

CCCCACCCCG AAGTGCTATC CTAGCTGCCA CTCCTGCAGA CCCGACCCGG CCCCACCACC       4549

AGAGTTTCAC CTCCCAGCAG TGATTCACAT TCCAGCATTG AAGGAGCCTC AGCTAACAGC       4609

CCTTCAAGGC CCAGCCTATA CCGGAGGCTG AGGCTCTGAT TTCCCTGTGA CACGCGTAGA       4669

CCTACTGCCC GACCCCAACT TCGGTGGCTT GGGATTTTGT GTTCTGCCAC CCTGAACCTC       4729

AGTAAGGGGG CTCGGACCAT CCAGACTGCC CCTACTGCCC ACAGCCCACC TGAGGACAAA       4789

GCTGGCACGG TCCCAGGGGT CCCAGGCCCG GCTGGAACCC ACACCTTGCC TTCAGCGACC       4849

TGGACTCTGG GTTCGGAGAG TGGCTTCGGG AGGCGTGGTT TCCGATGGGC GTGCTCTGGA       4909

ACGTGCTCGC CTGAACCAAC CTGTGTACAC TGGCCAGGAA TCACGGCCAC CAGAGCTCGG       4969

ACCTGACAGA GCCCTCAGCA GCCCCTCCTA GACCAACGTA CCCATTACAG AGAGGAGACA       5029

GTGACACAGA GGAGAGGAGA CTTGTCCCAG GTCCCTCAGC TGCTGTGAGG GCGGCCCTGG       5089

TGCCCCTTCC AGGCTGGGCA TCCCAGTAGC AGCAGGGGAC CCGGGGGTGG GGACACAGGC       5149

CCCGCCCTCC CTGGGAGGCA GGAAGCAGCT CTCAAATAAA CTGTTCTAAG TATGATACAG       5209

GAGTGATACA TGTGTGAAGA GAAGCCCTTA GGTGGGGGCA CAGAGTGTCT GGGTGAGGGG       5269
```

```
GGTCAGGGTC ACATCAGGAG GTTAGGGAGG GGTTGATGAA GGGCTGACGT TGAGCAAAGA      5329

CCAAAGGCAA CTCAGAAGGA CAGTGGTGCA GGACTGGGTG TGGTCAGCAG GGGGACTGGT      5389

TGGGGGATCC                                                              5399
```

( 2 ) INFORMATION FOR SEQ ID NO:10:

( i ) SEQUENCE CHARACTERISTICS:
        ( A ) LENGTH: 533 amino acids
        ( B ) TYPE: amino acid
        ( D ) TOPOLOGY: linear ( x i ) SEQUENCE DESCRIPTION: SEQ ID NO:10:

```
Met  Gln  Gly  Ala  Cys  Val  Leu  Leu  Leu  Leu  Gly  Leu  His  Leu  Gln  Leu
 1              5                        10                       15

Ser  Leu  Gly  Leu  Val  Pro  Val  Glu  Glu  Asp  Pro  Ala  Phe  Trp  Asn
              20                       25                       30

Arg  Gln  Ala  Ala  Gln  Ala  Leu  Asp  Val  Ala  Lys  Lys  Leu  Gln  Pro  Ile
            35                       40                       45

Gln  Thr  Ala  Ala  Lys  Asn  Val  Ile  Leu  Phe  Leu  Gly  Asp  Gly  Met  Gly
            50                       55                       60

Val  Pro  Thr  Val  Thr  Ala  Thr  Arg  Ile  Leu  Lys  Gly  Gln  Met  Asn  Gly
 65                       70                       75                       80

Lys  Leu  Gly  Pro  Glu  Thr  Pro  Leu  Ala  Met  Asp  Gln  Phe  Pro  Tyr  Val
                     85                       90                       95

Ala  Leu  Ser  Lys  Thr  Tyr  Asn  Val  Asp  Arg  Gln  Val  Pro  Asp  Ser  Ala
                  100                      105                      110

Gly  Thr  Ala  Thr  Ala  Tyr  Leu  Cys  Gly  Val  Lys  Gly  Asn  Tyr  Arg  Thr
                  115                      120                      125

Ile  Gly  Val  Ser  Ala  Ala  Ala  Arg  Tyr  Asn  Gln  Cys  Lys  Thr  Thr  Arg
            130                      135                      140

Gly  Asn  Glu  Val  Thr  Ser  Val  Met  Asn  Arg  Ala  Lys  Lys  Ala  Gly  Lys
 145                      150                      155                      160

Ser  Val  Gly  Val  Val  Thr  Thr  Thr  Arg  Val  Gln  His  Ala  Ser  Pro  Ala
                       165                      170                      175

Gly  Ala  Tyr  Ala  His  Thr  Val  Asn  Arg  Asn  Trp  Tyr  Ser  Asp  Ala  Asp
                  180                      185                      190

Leu  Pro  Ala  Asp  Ala  Gln  Met  Asn  Gly  Cys  Gln  Asp  Ile  Ala  Ala  Gln
            195                      200                      205

Leu  Val  Asn  Asn  Met  Asp  Ile  Asp  Val  Ile  Leu  Gly  Gly  Gly  Arg  Lys
            210                      215                      220

Tyr  Met  Phe  Pro  Val  Gly  Thr  Pro  Asp  Pro  Glu  Tyr  Pro  Asp  Asp  Ala
 225                      230                      235                      240

Ser  Val  Asn  Gly  Val  Arg  Lys  Arg  Lys  Gln  Asn  Leu  Val  Gln  Ala  Trp
                       245                      250                      255

Gln  Ala  Lys  His  Gln  Gly  Ala  Gln  Tyr  Val  Trp  Asn  Arg  Thr  Ala  Leu
                  260                      265                      270

Leu  Gln  Ala  Ala  Asp  Asp  Ser  Ser  Val  Thr  His  Leu  Met  Gly  Leu  Phe
            275                      280                      285

Glu  Pro  Ala  Asp  Met  Lys  Tyr  Asn  Val  Gln  Gln  Asp  His  Thr  Lys  Asp
            290                      295                      300

Pro  Thr  Leu  Gln  Glu  Met  Thr  Glu  Val  Ala  Leu  Arg  Val  Val  Ser  Arg
 305                      310                      315                      320

Asn  Pro  Arg  Gly  Phe  Tyr  Leu  Phe  Val  Glu  Gly  Gly  Arg  Ile  Asp  His
                       325                      330                      335

Gly  His  His  Asp  Asp  Lys  Ala  Tyr  Met  Ala  Leu  Thr  Glu  Ala  Gly  Met
```

|     |     |     |     |     |     | 340 |     |     |     |     |     | 345 |     |     |     |     |     | 350 |     |     |
| --- | --- | --- | --- | --- | --- | --- | --- | --- | --- | --- | --- | --- | --- | --- | --- | --- | --- | --- | --- | --- |

Phe Asp Asn Ala Ile Ala Lys Ala Asn Glu Leu Thr Ser Glu Leu Asp
    355                         360                  365

Thr Leu Ile Leu Val Thr Ala Asp His Ser His Val Phe Ser Phe Gly
    370                         375                         380

Gly Tyr Thr Leu Arg Gly Thr Ser Ile Phe Gly Leu Ala Pro Ser Lys
385                    390                      395                  400

Ala Leu Asp Ser Lys Ser Tyr Thr Ser Ile Leu Tyr Gly Asn Gly Pro
                405                      410                      415

Gly Tyr Ala Leu Gly Gly Gly Ser Arg Pro Asp Val Asn Asp Ser Thr
            420                      425                    430

Ser Glu Asp Pro Ser Tyr Gln Gln Gln Ala Ala Val Pro Gln Ala Ser
        435                     440                    445

Glu Thr His Gly Gly Glu Asp Val Ala Val Phe Ala Arg Gly Pro Gln
    450                       455                  460

Ala His Leu Val His Gly Val Glu Glu Glu Thr Phe Val Ala His Ile
465                    470                      475                  480

Met Ala Phe Ala Gly Cys Val Glu Pro Tyr Thr Asp Cys Asn Leu Pro
            485                      490                    495

Ala Pro Thr Thr Ala Thr Ser Ile Pro Asp Ala Ala His Leu Ala Ala
            500                      505                  510

Ser Pro Pro Pro Leu Ala Leu Leu Ala Gly Ala Met Leu Leu Leu Leu
        515                     520                    525

Ala Pro Thr Leu Tyr
    530

( 2 ) INFORMATION FOR SEQ ID NO:11:

( i ) SEQUENCE CHARACTERISTICS:
        ( A ) LENGTH: 540 amino acids
        ( B ) TYPE: amino acid
        ( D ) TOPOLOGY: linear ( x i ) SEQUENCE DESCRIPTION: SEQ ID NO:11:

Met Gln Gly Asp Trp Val Leu Leu Leu Leu Gly Leu Arg Ile His
1                  5                        10                    15

Leu Ser Phe Gly Val Ile Pro Val Glu Glu Asn Pro Val Phe Trp
            20                    25                  30

Asn Gln Lys Ala Lys Glu Ala Leu Asp Val Ala Lys Lys Leu Gln Pro
        35                     40                  45

Ile Gln Thr Ser Ala Lys Asn Leu Ile Leu Phe Leu Gly Asp Gly Met
    50                     55                      60

Gly Val Pro Thr Val Thr Ala Thr Arg Ile Leu Lys Gly Gln Leu Gly
65                      70                      75                  80

Gly His Leu Gly Pro Glu Thr Pro Leu Ala Met Asp His Phe Pro Phe
            85                      90                  95

Thr Ala Leu Ser Lys Thr Tyr Asn Val Asp Arg Gln Val Pro Asp Ser
            100                      105                110

Ala Gly Thr Ala Thr Ala Tyr Leu Cys Gly Val Lys Ala Asn Tyr Lys
                115                      120                  125

Thr Ile Gly Val Ser Ala Ala Ala Arg Phe Asn Gln Cys Asn Ser Thr
    130                     135                      140

Phe Gly Asn Glu Val Phe Ser Val Met His Arg Ala Lys Lys Ala Gly
145                    150                      155                  160

Lys Ser Val Gly Val Val Thr Thr Thr Arg Val Gln His Ala Ser Pro
                165                      170                  175

```
Ala Gly Thr Tyr Ala His Thr Val Asn Arg Asp Trp Tyr Ser Asp Ala
        180             185                     190

Asp Met Pro Ser Ser Ala Leu Gln Glu Gly Cys Lys Asp Ile Ala Thr
        195             200                     205

Gln Leu Ile Ser Asn Met Asp Ile Asp Val Ile Leu Gly Gly Gly Arg
210             215                     220

Lys Phe Met Phe Pro Lys Gly Thr Pro Asp Pro Glu Tyr Pro Gly Asp
225             230                     235                     240

Ser Asp Gln Ser Gly Val Arg Leu Asp Ser Arg Asn Leu Val Glu Glu
                245                     250                     255

Trp Leu Ala Lys Tyr Gln Gly Thr Arg Tyr Val Trp Asn Arg Glu Gln
            260                     265                     270

Leu Met Gln Ala Ser Gln Asp Pro Ala Val Thr Arg Leu Met Gly Leu
        275                     280                     285

Phe Glu Pro Thr Glu Met Lys Tyr Asp Val Asn Arg Asn Ala Ser Ala
        290                     295                     300

Asp Pro Ser Leu Ala Glu Met Thr Glu Val Ala Val Arg Leu Leu Ser
305                     310                     315                     320

Arg Asn Pro Gln Gly Phe Tyr Leu Phe Val Glu Gly Gly Arg Ile Asp
                325                     330                     335

Gln Gly His His Ala Gly Thr Ala Tyr Leu Ala Leu Thr Glu Ala Val
            340                     345                     350

Met Phe Asp Ser Ala Ile Glu Lys Ala Ser Gln Leu Thr Asn Glu Lys
        355                     360                     365

Asp Thr Leu Thr Leu Ile Thr Ala Asp His Ser His Val Phe Ala Phe
370                     375                     380

Gly Gly Tyr Thr Leu Arg Gly Thr Ser Ile Phe Gly Leu Ala Pro Leu
385                     390                     395                     400

Asn Ala Gln Asp Gly Lys Ser Tyr Thr Ser Ile Leu Tyr Gly Asn Gly
                405                     410                     415

Pro Gly Tyr Val Leu Asn Ser Gly Asn Arg Pro Asn Val Thr Asp Ala
            420                     425                     430

Glu Ser Gly Asp Val Asn Tyr Lys Gln Gln Ala Ala Val Pro Leu Ser
        435                     440                     445

Ser Glu Thr His Gly Gly Glu Asp Val Ala Ile Phe Ala Arg Gly Pro
    450                     455                     460

Gln Ala His Leu Val His Gly Val Gln Glu Gln Asn Tyr Ile Ala His
465                     470                     475                     480

Val Met Ala Phe Ala Gly Cys Leu Glu Pro Tyr Thr Asp Cys Gly Leu
                485                     490                     495

Ala Pro Pro Ala Asp Glu Asn Arg Pro Thr Thr Pro Val Gln Asn Ser
            500                     505                     510

Ala Ile Thr Met Asn Asn Val Leu Leu Ser Leu Gln Leu Leu Val Ser
        515                     520                     525

Met Leu Leu Leu Val Gly Thr Ala Leu Val Val Ser
530                     535                     540
```

( 2 ) INFORMATION FOR SEQ ID NO:12:

( i ) SEQUENCE CHARACTERISTICS:
    ( A ) LENGTH: 559 amino acids
    ( B ) TYPE: amino acid
    ( D ) TOPOLOGY: linear ( x i ) SEQUENCE DESCRIPTION: SEQ ID NO:12:

| | | | | | | | | | | | | | | |
|---|---|---|---|---|---|---|---|---|---|---|---|---|---|---|
| Met 1 | Gln | Gly | Pro | Trp 5 | Val | Leu | Leu | Leu 10 | Leu | Gly | Leu | Arg | Leu 15 | Leu |
| Ser | Leu | Ser | Val 20 | Ile | Pro | Val | Glu 25 | Glu | Asn | Pro | Ala | Phe 30 | Trp | Asn |
| Lys | Lys | Ala 35 | Ala | Glu | Ala | Leu | Asp 40 | Ala | Ala | Lys | Lys 45 | Leu | Gln | Pro | Ile |
| Gln | Thr 50 | Ser | Ala | Lys | Asn | Leu 55 | Ile | Ile | Phe | Leu | Gly 60 | Asp | Gly | Met | Gly |
| Val 65 | Pro | Thr | Val | Thr 70 | Ala | Thr | Arg | Ile | Leu 75 | Lys | Gly | Gln | Leu | Glu | Gly 80 |
| His | Leu | Gly | Pro | Glu 85 | Thr | Pro | Leu | Ala | Met 90 | Asp | Arg | Phe | Pro | Tyr 95 | Met |
| Ala | Leu | Ser | Lys 100 | Thr | Tyr | Ser | Val | Asp 105 | Arg | Gln | Val | Pro | Asp 110 | Ser | Ala |
| Ser | Thr | Ala 115 | Thr | Ala | Tyr | Leu | Cys 120 | Gly | Val | Lys | Thr | Asn 125 | Tyr | Lys | Thr |
| Ile | Gly 130 | Leu | Ser | Ala | Ala | Ala 135 | Arg | Phe | Asp | Gln | Cys 140 | Asn | Thr | Thr | Phe |
| Gly 145 | Asn | Glu | Val | Phe | Ser 150 | Val | Met | Tyr | Arg | Ala 155 | Lys | Lys | Ala | Gly | Lys 160 |
| Ser | Val | Gly | Val | Val 165 | Thr | Thr | Thr | Arg | Val 170 | Gln | His | Ala | Ser | Pro 175 | Ser |
| Gly | Thr | Tyr | Val 180 | His | Thr | Val | Asn | Arg 185 | Asn | Trp | Tyr | Gly | Asp 190 | Ala | Asp |
| Met | Pro | Ala 195 | Ser | Ala | Leu | Arg | Glu 200 | Gly | Cys | Lys | Asp | Ile 205 | Ala | Thr | Gln |
| Leu | Ile 210 | Ser | Asn | Met | Asp | Ile 215 | Asn | Val | Ile | Leu | Gly 220 | Gly | Gly | Arg | Lys |
| Tyr 225 | Met | Phe | Pro | Ala | Gly 230 | Thr | Pro | Asp | Pro | Glu 235 | Tyr | Pro | Asn | Asp | Ala 240 |
| Asn | Glu | Thr | Gly | Thr 245 | Arg | Leu | Asp | Gly | Arg 250 | Asn | Leu | Val | Gln | Glu 255 | Trp |
| Leu | Ser | Lys | His 260 | Gln | Gly | Ser | Gln | Tyr 265 | Val | Trp | Asn | Arg | Glu 270 | Gln | Leu |
| Ile | Gln | Lys 275 | Ala | Gln | Asp | Pro | Ser 280 | Val | Thr | Tyr | Leu | Met 285 | Gly | Leu | Phe |
| Glu | Pro 290 | Val | Asp | Thr | Lys | Phe 295 | Asp | Ile | Gln | Arg | Asp 300 | Pro | Leu | Met | Asp |
| Pro 305 | Ser | Leu | Lys | Asp | Met 310 | Thr | Glu | Thr | Ala | Val 315 | Lys | Val | Leu | Ser | Arg 320 |
| Asn | Pro | Lys | Gly | Phe 325 | Tyr | Leu | Phe | Val | Glu 330 | Gly | Gly | Arg | Ile | Asp 335 | Arg |
| Gly | His | His | Leu 340 | Gly | Thr | Ala | Tyr | Leu 345 | Ala | Leu | Thr | Glu | Ala 350 | Val | Met |
| Phe | Asp | Leu 355 | Ala | Ile | Glu | Arg | Ala 360 | Ser | Gln | Leu | Thr | Ser 365 | Glu | Arg | Asp |
| Thr | Leu 370 | Thr | Ile | Val | Thr | Ala 375 | Asp | His | Ser | His | Val 380 | Phe | Ser | Phe | Gly |
| Gly 385 | Tyr | Thr | Leu | Arg | Gly 390 | Thr | Ser | Ile | Phe | Gly 395 | Leu | Ala | Pro | Leu | Asn 400 |
| Ala | Leu | Asp | Gly | Lys 405 | Pro | Tyr | Thr | Ser | Ile 410 | Leu | Tyr | Gly | Asn | Gly 415 | Pro |
| Gly | Tyr | Val | Gly 420 | Gly | Thr | Gly | Glu | Arg 425 | Pro | Asn | Val | Thr | Ala 430 | Ala | Glu |

```
Ser  Ser  Gly  Ser  Ser  Tyr  Arg  Arg  Gln  Ala  Ala  Val  Pro  Val  Lys  Ser
          435                 440                     445

Glu  Thr  His  Gly  Gly  Glu  Asp  Val  Ala  Ile  Phe  Ala  Arg  Gly  Pro  Gln
     450                 455                     460

Ala  His  Leu  Val  His  Gly  Val  Gln  Glu  Gln  Asn  Tyr  Ile  Ala  His  Val
465                      470                     475                          480

Met  Ala  Ser  Ala  Gly  Cys  Leu  Glu  Pro  Tyr  Thr  Asp  Cys  Gly  Leu  Ala
                    485                 490                          495

Pro  Pro  Ala  Asp  Glu  Ser  Gln  Thr  Thr  Thr  Thr  Thr  Arg  Gln  Thr  Thr
               500                 505                          510

Ile  Thr  Thr  Thr  Thr  Thr  Thr  Thr  Thr  Thr  Thr  Thr  Pro  Val  His
          515                      520                     525

Asn  Ser  Ala  Arg  Ser  Leu  Gly  Pro  Ala  Thr  Ala  Pro  Leu  Ala  Leu  Ala
     530                 535                     540

Leu  Leu  Ala  Gly  Met  Leu  Met  Leu  Leu  Leu  Gly  Ala  Pro  Ala  Glu
545                      550                 555
```

(2) INFORMATION FOR SEQ ID NO:13:

(i) SEQUENCE CHARACTERISTICS:
(A) LENGTH: 528 amino acids
(B) TYPE: amino acid
(D) TOPOLOGY: linear (xi) SEQUENCE DESCRIPTION: SEQ ID NO:13:

```
Met  Gln  Gly  Pro  Trp  Val  Leu  Leu  Leu  Leu  Gly  Leu  Arg  Leu  Gln  Leu
1                   5                    10                      15

Ser  Leu  Gly  Val  Ile  Pro  Ala  Glu  Glu  Glu  Asn  Pro  Ala  Phe  Trp  Asn
               20                  25                      30

Arg  Gln  Ala  Ala  Glu  Ala  Leu  Asp  Ala  Ala  Lys  Lys  Leu  Gln  Pro  Ile
          35                  40                      45

Gln  Lys  Val  Ala  Lys  Asn  Leu  Ile  Leu  Phe  Leu  Gly  Asp  Gly  Leu  Gly
     50                  55                      60

Val  Pro  Thr  Val  Thr  Ala  Thr  Arg  Ile  Leu  Lys  Gly  Gln  Lys  Asn  Gly
65                       70                  75                           80

Lys  Leu  Gly  Pro  Glu  Thr  Pro  Leu  Ala  Met  Asp  Arg  Phe  Pro  Tyr  Leu
               85                  90                      95

Ala  Leu  Ser  Lys  Thr  Tyr  Asn  Val  Asp  Arg  Gln  Val  Pro  Asp  Ser  Ala
               100                 105                     110

Ala  Thr  Ala  Thr  Ala  Tyr  Leu  Cys  Gly  Val  Lys  Ala  Asn  Phe  Gln  Thr
          115                 120                     125

Ile  Gly  Leu  Ser  Ala  Ala  Ala  Arg  Phe  Asn  Gln  Cys  Asn  Thr  Thr  Arg
     130                 135                     140

Gly  Asn  Glu  Val  Ile  Ser  Val  Met  Asn  Arg  Ala  Lys  Gln  Ala  Gly  Lys
145                      150                 155                          160

Ser  Val  Gly  Val  Val  Thr  Thr  Thr  Arg  Val  Gln  His  Ala  Ser  Pro  Ala
                    165                 170                     175

Gly  Thr  Tyr  Ala  His  Thr  Val  Asn  Arg  Asn  Trp  Tyr  Ser  Asp  Ala  Asp
               180                 185                     190

Met  Pro  Ala  Ser  Ala  Arg  Gln  Glu  Gly  Cys  Gln  Asp  Ile  Ala  Thr  Gln
          195                 200                     205

Leu  Ile  Ser  Asn  Met  Asp  Ile  Asp  Val  Ile  Leu  Gly  Gly  Gly  Arg  Lys
     210                 215                     220

Tyr  Met  Phe  Pro  Met  Gly  Thr  Pro  Asp  Pro  Glu  Tyr  Pro  Ala  Asp  Ala
225                      230                 235                          240
```

-continued

| | | | | | | | | | | | | | | | |
|---|---|---|---|---|---|---|---|---|---|---|---|---|---|---|---|
| Ser | Gln | Asn | Gly | Ile 245 | Arg | Leu | Asp | Gly | Lys 250 | Asn | Leu | Val | Gln | Glu 255 | Trp |
| Leu | Ala | Lys | His 260 | Gln | Gly | Ala | Trp | Tyr 265 | Val | Trp | Asn | Arg | Thr 270 | Glu | Leu |
| Met | Glu | Ala 275 | Ser | Leu | Asp | Gln | Ser 280 | Val | Thr | His | Leu | Met 285 | Gly | Leu | Phe |
| Glu | Pro 290 | Gly | Asp | Thr | Lys | Tyr 295 | Glu | Ile | His | Arg | Asp 300 | Pro | Thr | Leu | Asp |
| Pro 305 | Ser | Leu | Met | Glu | Met 310 | Thr | Glu | Ala | Ala | Leu 315 | Arg | Leu | Leu | Ser | Arg 320 |
| Asn | Pro | Arg | Gly | Phe 325 | Tyr | Leu | Phe | Val | Glu 330 | Gly | Gly | Arg | Ile | Asp 335 | His |
| Gly | His | His | Glu 340 | Gly | Val | Ala | Tyr | Gln 345 | Ala | Leu | Thr | Glu | Ala 350 | Val | Met |
| Phe | Asp | Asp 355 | Ala | Ile | Glu | Arg | Ala 360 | Gly | Gln | Leu | Thr | Ser 365 | Glu | Glu | Asp |
| Thr | Leu 370 | Thr | Leu | Val | Thr | Ala 375 | Asp | His | Ser | His | Val 380 | Phe | Ser | Phe | Gly |
| Gly 385 | Tyr | Thr | Leu | Arg | Gly 390 | Ser | Ser | Ile | Phe | Gly 395 | Leu | Ala | Pro | Ser | Lys 400 |
| Ala | Gln | Asp | Ser | Lys 405 | Ala | Tyr | Thr | Ser | Thr 410 | Leu | Tyr | Gly | Asn | Gly 415 | Pro |
| Gly | Tyr | Val | Phe 420 | Asn | Ser | Gly | Val | Arg 425 | Pro | Asp | Val | Asn | Glu 430 | Ser | Glu |
| Ser | Gly | Ser 435 | Pro | Asp | Tyr | Gln | Gln 440 | Gln | Ala | Ala | Val | Pro 445 | Leu | Ser | Ser |
| Glu | Thr 450 | His | Gly | Gly | Glu | Asp 455 | Val | Ala | Val | Phe | Ala 460 | Arg | Gly | Pro | Gln |
| Ala 465 | His | Leu | Val | His | Gly 470 | Val | Gln | Glu | Gln | Ser 475 | Phe | Val | Ala | His | Val 480 |
| Met | Ala | Phe | Ala | Ala 485 | Cys | Leu | Glu | Pro | Tyr 490 | Thr | Ala | Cys | Asp | Leu 495 | Ala |
| Pro | Pro | Ala | Cys 500 | Thr | Thr | Asp | Ala | Ala 505 | His | Pro | Val | Ala | Ala 510 | Ser | Leu |
| Pro | Leu | Leu 515 | Ala | Gly | Thr | Leu | Leu 520 | Leu | Leu | Gly | Ala | Ser 525 | Ala | Ala | Pro |

NUCLEIC ACID ENCODING CALF INTESTINAL ALKALINE PHOSPHATASE

This application is a continuation of application Ser. No. 08/213,371, filed Mar. 14, 1994, which is a continuation of application Ser. No. 07/849,219, filed Mar. 10, 1992, both now abandoned.

The invention was made, in part, with government support under grants CA48560 and CA30199 awarded by the National Institutes of Health. The United States government has certain rights in this invention.

BACKGROUND OF THE INVENTION

The present invention relates to recombinant calf intestinal alkaline phosphatase and more particularly to isolated nucleic acids encoding the recombinant form of calf intestinal alkaline phosphatase.

Alkaline phosphatases (APs) are a family of functionally related enzymes named after the tissues in which they predominately appear. Such enzymes carry out hydrolase/transferase reactions on phosphate-containing substrates at a high pH optimum. The exact role of APs in biological processes remains poorly defined.

In humans and other higher animals, the AP family contains four members that are each encoded by a separate gene locus as reviewed in Millan, *Anticancer Res.* 8:995–1004 (1988) and Harris, *Clin. Chem. Acta* 186:133–150 (1989). The alkaline phosphatase family includes the tissue specific APs (placental AP, germ cell AP and intestinal AP) and the tissue non-specific AP found predominately in the liver, bone and kidney.

Intestinal alkaline phosphatase (IAP) derived from humans has been extensively characterized. As with all known APs, human IAP appears as a dimer, which is referred to as p75/150 in Latham & Stanbridge, *P.N.A.S. (USA)* 87:1263–1267 (1990). A cDNA clone for human adult IAP has been isolated from a λgt11 expression library. This cDNA clone is 2513 base pairs in length and contains an open reading frame that encodes a 528 amino acid polypeptide as described in Henthorn et al., *P.N.A.S. (USA)* 84:1234–1238 (1987). IAP has also been found in other species, such as mice, cows, and fish as reported in McComb et al., *Alkaline Phosphatases* (Plenum, New York, 1989).

Generally, alkaline phosphatases are useful diagnostically in liver and bone disorders as described in McComb et al., supra, or for certain cancers as reviewed in Millan, *Prog. Clin. Biol. Res.*, 344:453–475 (1990). APs are also useful as reagents in molecular biology. Of the known APs, bovine IAP has the highest catalytic activity. This property has made bovine IAP highly desirable for such biotechnological applications as enzyme-conjugates for use as diagnostics reagents or dephosphorylation of DNA, for example.

The isozymes of bovine IAP (b.IAP), including calf IAP, adult bovine IAP, and a tissue non-specific isozyme extracted from the small intestines, have been characterized by Besman & Coleman, *J. Biol. Chem.*, 260:1190–1193 (1985). Although it is possible to purify naturally-occurring calf IAP extracted from intestinal tissues, it is technically very difficult to obtain an enzyme preparation of reproducible quality and purity. Generally, the enzymes are extracted from bovine intestines obtained from slaughter houses. Since the sacrificed animals are not of the same age, the proportion of the known b.IAP isozymes will vary significantly among the purified extracts.

Moreover, the intestine is known to contain high amounts of peptidases and glycosidases that degrade the naturally occurring IAP. Since the time from slaughter to enzyme extraction varies greatly, the amount of degradation will also vary greatly, resulting in a mixture of intact and several degradation products. Accordingly, the known methods of purifying IAP from naturally-occurring sources produce microheterogeneity in the purified IAP preparations. These partially degraded IAP molecules are technically difficult to separate from the native intact IAP molecules.

Due in part to the technical problems of separating intact b.IAP from degraded or partially processed calf IAP and the minute quantities of purified intact b.IAP that can be obtained from naturally-occurring sources, it has been difficult to determine the amino acid sequence encoding calf IAP. In addition, attempts to crystalize the IAP protein to determine the three-dimensional structure from the natural source has been hampered because of such microheterogeneity of the enzyme obtained from natural sources. It has only been possible to obtain small crystals of the natural enzyme, which are of insufficient quality for crystallographic studies.

Thus, a need exists for a homogeneous source of calf intestine alkaline phosphatase. Such a source would ideally provide an ample supply of pure, intact calf IAP for research and commercial use without time-consuming and labor intensive procedures. The present invention satisfies this need and provides related advantages as well.

SUMMARY OF THE INVENTION

The present invention generally relates to recombinant calf intestinal alkaline phosphatase (calf IAP) having an amino acid sequence substantially the same as naturally occurring calf IAP or its active fragments. The invention further provides isolated nucleic acids encoding such polypeptides. Vectors containing these nucleic acids and recombinant host cells transformed or transfected with such vectors are also provided.

Nucleic acid probes having nucleotide sequences complementary to a portion of the nucleotide sequence encoding calf IAP are also provided. Such probes can be used for the detection of nucleic acids encoding calf IAP or active fragments thereof.

The present invention further provides a multifunctional polypeptide containing an amino acid sequence of calf IAP and a second amino acid sequence having specific reactivity with a desired ligand. The second amino acid sequence can encode, for example, an antibody sequence when the desired ligand is an antigen.

The pure recombinant polypeptides of the present invention, including the multifunctional polypeptides, are particularly useful in methods for detecting the presence of antigens or other ligands in substances, such as fluid samples and tissues. Such diagnostic methods can be used for in vitro detection of such ligands.

BRIEF DESCRIPTION OF THE DRAWINGS

FIG. 1 shows the full length genomic (SEQ ID NO: 9) sequence of calf IAP and the deduced amino acid (SEQ ID NO: 10) sequence.

FIG. 3 shows a comparison of IAPs from calf (b.IAP; SEQ ID NO: 10), rat (r.IAP; SEQ ID NO: 11), mouse (m.IAP; SEQ ID NO: 12), and human (h.IAP; SEQ ID NO: 13).

DETAILED DESCRIPTION OF THE INVENTION

Figure 2:
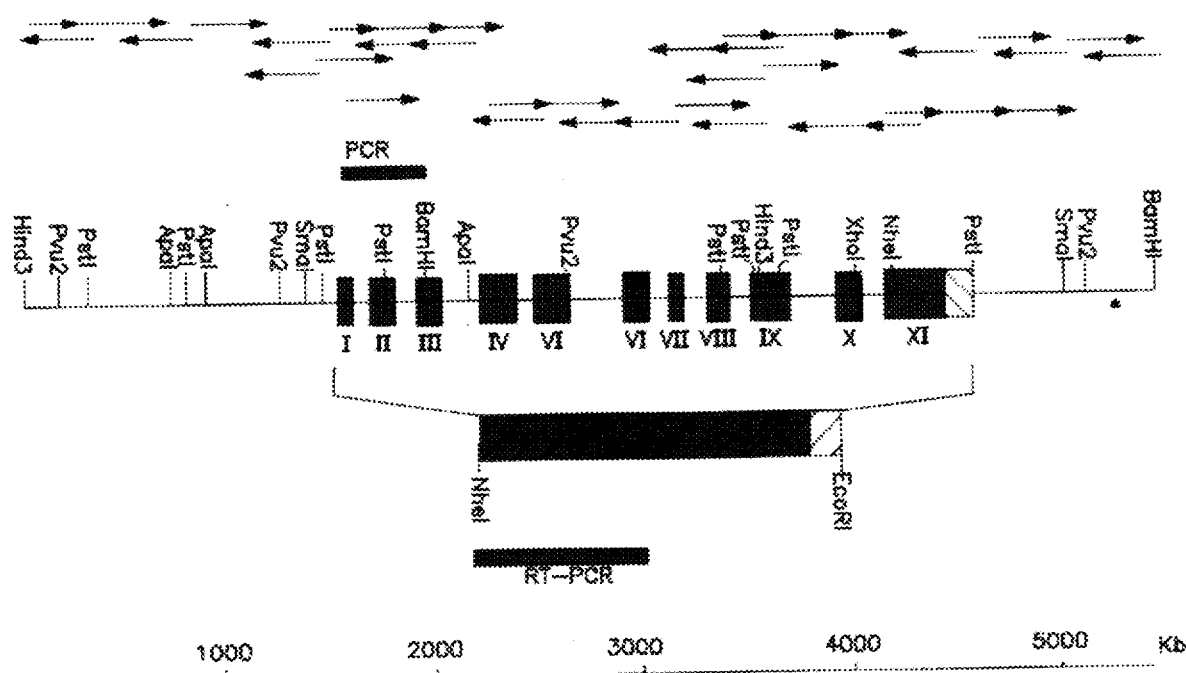
FIG. 2 shows the restriction map of the entire calf IAP gene and the full length cDNA.

The present invention relates to the elucidation of the calf intestinal alkaline phosphatase gene. More specifically, the invention relates to the nucleotide sequence of the region of the gene encoding the enzyme.

Previous attempts to produce a full length cDNA or a complete genomic clone for calf IAP have been unsuccessful. RNA extracted from bovine intestinal tissues are not fully processed (i.e., incompletely spliced RNA) or are quickly degraded after death. As such, only fragments of the genome coding region could be obtained.

It was through the extensive experimentation as set forth in the examples below that the full length cDNA clone of calf IAP was determined. Accordingly, the present invention is directed to isolated nucleic acids comprising the nucleotide sequence encoding calf IAP or an active fragment thereof having the enzymatic activity of the intact calf IAP. The nucleic acids can be DNA, cDNA or RNA.

The nucleic acid can have the nucleotide sequence substantially the same as the sequence identified in FIG. 1, which shows the complete coding region of the genomic sequence of calf IAP. This nucleic acid (5.4 kb) contains 11 exons separated by 10 small introns at positions identical to those of other members of the tissue-specific AP family. Additionally, a 1.5 kb of the 5' sequence contains putative regulatory elements having homology to human and mouse IAP promoter sequences.

As used herein, the term "substantially the sequence" means the described nucleotide or amino acid sequence or other sequences having one or more additions, deletions or substitutions that do not substantially affect the ability of the sequence to encode a polypeptide having a desired activity, such as calf IAP or its active fragments. Thus, modifications that do not destroy the encoded enzymatic activity are contemplated.

As used herein, an active fragment of calf IAP refers to portions of the intact enzyme that substantially retains the enzymatic activity of the intact enzyme. The retention of activity can be readily determined using methods known to those skilled in the art.

The terms "isolated" and "substantially purified" are used interchangeably and mean the polypeptide or nucleic acid is essentially free of other biochemical moieties with which it is normally associated in nature. Recombinant polypeptides are generally considered to be substantially purified.

The present invention further relates to expression vectors into which the coding region of the calf IAP gene can be subcloned. "Vectors" as used herein are capable of expressing nucleic acid sequences when such sequences are operationally linked to other sequences capable of effecting their expression. These expression vectors must be replicable in the host organisms either as episomes or as an integral part of the chromosomal DNA. Lack of replicability would render them effectively inoperable. In general, useful vectors in recombinant DNA techniques are often in the form of plasmids, which refer to circular double stranded DNA loops which are not bound to the chromosome in their vector form. Suitable expression vectors can be plasmids such as, for example, pcDNA1 (Invitrogen, San Diego, Calif.).

A number of procaryotic expression vectors are known in the art, such as those disclosed, for example, in U.S. Pat. Nos. 4,440,859; 4,436,815; 4,431,740; 4,431,739; 4,428,941; 4,425,437; 4,418,149; 4,411,994 and 4,342,832, all incorporated herein by reference. Eucaryotic systems and yeast expression vectors can also be used as described, for example, in U.S. Pat. Nos. 4,446,235; 4,443,539; and 4,430,428, all incorporated herein by reference.

The vectors can be used to transfect or transform suitable host cells by various methods known in the art, such as described in Sambrook et al., *Molecular Cloning: A Laboratory Manual*, Cold Spring Harbor, N.Y. (1989). Such host cells can be either eucaryotic or procaryotic cells. Examples of such hosts include chinese hamster ovary (CHO) cells, *E. Coli* and baculovirus infected insect cells. As used herein, "host cells" or "recombinant host cells" refer not only to the particular subject cell but to the progeny or potential progeny of such cell. Because certain modifications may occur in succeeding generations due to either mutation or environmental influences, such progeny may not, in fact, be identical to the parent cell, but are still included within the scope of the term as used herein.

The present invention further relates to recombinant proteins or polypeptides produced by the recombinant host cells of the present invention. The recombinant calf IAP protein has been characterized in terms of its heat stability up to about 50° C., electrophoretic and isoelectric focusing (IEF) behavior and kinetic parameters. The recombinant calf IAP protein of the present invention demonstrated displayed kinetic properties comparable to commercially available purified calf IAP, while showing less heterogenicity than the commercial enzymes in polyacrylamide gel electrophoresis and IEF, as described in the examples below.

Methods for obtaining or isolating recombinant calf IAP or active fragments are also provided. Such methods include culturing the recombinant host cells in a suitable growth medium. The protein or active fragments can thereafter be isolated from the cells by methods known in the art. If the expression system secretes calf IAP protein into growth media, the protein can be purified directly from cell-free media. If the protein is not secreted, it can be isolated from cell lysates. The selection of the appropriate growth conditions and recovery methods are within the knowledge of one skilled in the art. Recombinant calf IAP or active fragments thereof can be unglycosylated or have a different glycosylation pattern than the native enzyme depending on the host that is used to prepare it.

The present invention further provides isolated nucleic acids containing a nucleotide sequence encoding calf IAP or an active fragment thereof and a second nucleotide sequence encoding a polypeptide having specific reactivity with a ligand. Such nucleic acids encode a chimeric or multifunctional polypeptide in which a region of the polypeptide has enzymatic activity conferred by the calf IAP sequence attached to a second region having specific reactivity with a particular ligand. Such multifunctional polypeptides are particularly useful in diagnostic assays for determining the presence or concentration of a particular ligand in a sample. The ligand can be, for example, a cancer marker, allergen, drug or other moiety having an ability to specifically bind with an antibody or antibody-like agent encoded by a multifunctional polypeptide of the present invention. For instance, the second nucleotide sequence can encode an anti-CEA antibody when the target ligand is CEA (carcinoembryonic antigen). The ligand can also be a fragment of DNA or other nucleic acids.

Nucleic acid probes specific for a portion of nucleotides that encode calf IAP can be used to detect nucleic acids specific to calf IAP for diagnostic purposes. Nucleic acid probes suitable for such purposes can be prepared from the cloned sequences or by synthesizing oligonucleotides that hybridize only with the homologous sequence under stringent conditions. The oligonucleotides can be synthesized by any appropriate method, such as by an automated DNA synthesizer.

The oligonucleotides can be used to detect DNA and mRNA or to isolate cDNA clones from libraries. The particular nucleotide sequences selected are chosen so as to correspond to the codons encoding a known amino acid sequence from the protein. Generally, an effective length of a probe is recognized in the art is about 14 to about 20 bases. Longer probes of about 25 to about 60 bases can also be used. A probe can be labelled, using labels and methods well known in the art, such as a radionucleotide or biotin, using standard procedures.

The purified recombinant calf IAP or its active fragments can be used for diagnostic purposes to determine the presence or concentration of a ligand in a sample. The sample can be a fluid or tissue specimen obtained, for example, from a patient suspected of being exposed to a particular antigen or DNA fragment. Those skilled in the art will recognize that any assay capable of using an enzyme-catalyzed system can be used in the detection methods of the present invention.

In the detection methods of the present invention:

(a) a sample is contacted with the recombinant calf IAP or an active fragment thereof attached to a reagent specifically reactive with the ligand to be detected;

(b) the sample is contacted with a detectable agent catalyzed by calf IAP; and (c) the binding of the sample to the reagent is detected, where binding indicates the presence of the ligand in the sample.

The methods can also be used to determine the concentration of a ligand in the sample by relating the amount of binding to the concentration of the ligand. To determine the concentration, the amount of binding can be compared to known concentrations of the ligand or to standardized measurements, such as slopes, determined from known concentrations of the ligand.

A variety of ligands can be detected by the present methods. The ligand can be, for example, a protein or polypeptide having antigenic properties or a nucleic acid, such as DNA or RNA.

Reagents reactive with such ligands can be antibodies or reactive fragments of such antibodies when the ligand is an antigen or antigen-like molecule. The reagent can also be a nucleotide probe that hybridizes or binds to a specific nucleic acid, such as DNA or RNA. Such probes can be oligonucleotides that are complementary to cDNA or genomic fragments of a ligand.

Procedures for attaching the enzymes to various reagents are well known in the art. Techniques for coupling enzymes to antibodies, for example, are described in Kennedy et al., Clin. Chim. Acta 70:1 (1976), incorporated herein by reference. Reagents useful for such coupling include, for example, glutaraldehyde, p-toluene diisocyanate, various carbodiimide reagents, p-benzoquinone m-periodate, N,N'-o-phenylenediamalemide and the like. Alternatively, the multifunctional polypeptides of the present invention can be used.

Suitable substrates for the biochemical detection of ligands according to the methods of the present invention include, for example, p-nitrophenylphosphate.

The recombinant form of calf IAP is also useful for the development of calf IAP having greater heat stability. By site directed mutagenesis, it is possible to modify the nucleic acid sequence encoding for the recombinant protein to obtain a heat stable calf IAP comparable to human placental IAP, which is known to be stable at about 65° C. Greater heat stability would allow the use of such a modified calf IAP in procedures requiring higher heating, such as Southern blotting, for example, which generally denatures many enzymes.

The following examples are intended to illustrate but not limit the invention.

EXAMPLE I

Libraries and Screening Procedures

Initially, a λgt11 cDNA library prepared from adult bovine intestine (Clontech Laboratories, Palo Alto, Calif.) was screened using a mouse IAP cDNA fragment described in Manes et al., *Genomics* 8:541–554 (1990) as a probe. A 2.1 kb unprocessed cDNA fragment and a 1.1 kb processed cDNA fragment, both isolated from this library, were used to screen a genomic library prepared from adult cow liver in EMBL3 SP6/T7 (Clontech Laboratories, Palo Alto, Calif.). Radiolabelling of probes with $^{32}P$ and identification and isolation of positive clones was done as described in Manes et al., supra, which is incorporated herein by reference. Large-scale phage DNA preparation was performed as described in Sambrook et al., supra, incorporated herein by reference.

Initially, one positive cDNA clone was obtained upon screening the λgt11 cDNA library with the mouse IAP cDNA fragment. Sequencing from the ends of the 2.1 kb cDNA fragment (R201) revealed an incomplete cDNA encoding exons VI through XI of an alkaline phosphatase gene as identified by sequence comparison to known AP genes. This cDNA fragment included all introns and revealed several STOP codons as well as two frameshifts in the putative coding region of the gene.

Although further sequence information of R201 suggested that it is possibly transcribed from a pseudogene, it was used as a probe for further screening of the λgt11 library. Two additional cDNA clones were subsequently isolated and identified as transcripts of another alkaline phosphatase gene. Again, one fragment of 0.8 kb length (BB203) turned out to be reverse transcribed from an incomplete and unprocessed RNA, whereas the other one, a cDNA fragment of 1.1 kb length (BB204), was derived from a partial but processed mRNA, extending from the end of exon V through exon XI, lacking a putative poly-adenylation site and a poly-A tail.

EXAMPLE II

Characterization of Genomic Clones and Sequence Analysis

Genomic DNA was isolated from adult cow liver and Southern blot analysis was performed using standard protocols as described in Sambrook et al., supra. Restriction enzymes were obtained from Gibco BRL, Boehringer Mannheim, and New England Biolabs. Twenty μg of genomic DNA were used per reaction. The blots were probed with the 2.1 kb unprocessed cDNA fragment, and washed under high stringency conditions (0.1×SSC at 65° C.).

Two bands in the genomic Southern were identified as fragments derived from the b.IAP gene. The only other non-human mammalian genome investigated extensively for tissues specific (TSAP) genes so far has been the murine genome, as reported in Manes et al., supra. Two murine TSAP genes, one termed embryonic AP (EAP), the other coding for IAP, and a pseudogene were cloned. In previous studies, it was shown that there are two TSAP genes expressed in the bovine genome according to Culp et al., *Biochem. Biophys. Acta* 831:330–334 (1985) and Besman & Coleman, supra. Similarly, two APs have been found expressed in the adult intestine of mice as reported in Hahnel et al., *Development* 110:555–564 (1990). Expression of AP in rat intestine appears to be even more complex (Ellakim et al., *Am. J. Physiol.* 159, 1.1:G93–98 (1990)). Identification of the b.IAP gene was possible by comparison of its deduced amino acid sequence with N-terminal sequences reported for both TSAP isozymes.

Since further screening of the cDNA library revealed no additional positive clones, both R201 and BB204 were used to screen an EMBL3 SP6/T7 genomic library. Three positive clones were obtained and analyzed by Southern blotting. Subsequent sequencing of several fragments from two of the clones showed that one contained the entire coding region for the b.IAP gene as identified by comparison of deduced amino acid sequence with sequences previously determined in Culp et al., supra and Besman & Coleman, supra. A 5.4 kb sequence from overlapping Hind III and BamH1 fragments of the clone containing the b.IAP gene are presented in FIG. 1. The other clone contained sequences identical (except for a few basepair changes) with R201.

Genomic clones were characterized and sequences were determined as described in Manes et al., supra. Nucleic acid and protein sequences were assembled and analyzed using the MacVector sequence analysis program (IBI, New Haven, Conn.).

EXAMPLE III

PCR Mutagenesis and Subcloning into pcDNA

A 23-mer primer ("MKNHE" (SEQ ID NO: 1): 5'-GCTAGCCATGCAGGGGGCCTGCG-3'(SEQ ID NO: 2)) was used to amplify base pairs 1497–1913 of the b.IAP gene which had been subcloned as a Hind III/BamH1 fragment into Bluescript-KS+ (Stratagene, San Diego, Calif.). MKNHE (SEQ ID NO: 1) had been designed to create a new Nhe I site by altering the three 5' nucleotides of the primer sequence compared to the genomic sequence to allow the easy subcloning into different expression vectors. The universal SK primer was used as complementary reverse primer in the performed polymerase chain reaction (PCR). The plasmid was heat denatured, annealed to the primers and subjected to 30 cycles of PCR amplification in an Automatic Thermocycler (MJ Research, Piscataway, N.J.). Times and temperatures were set as follows: annealing at 40° C. for 30 seconds, extension for 3 minutes at 72° C. and denaturing at 95° C. for 30 seconds. The amplified fragment was directly subcloned into the "T-modified" EcoRV site of Bluescript as described in Marchuk et al., *Nucl. Acids Res.* 19:1154 (1990), incorporated herein by reference, in the orientation of b-galactosidase transcription.

EXAMPLE IV

Sequencing of the Amplified Fragment

The amplified fragment was sequenced using the universal T3 and T7 primers in the Sanger dideoxy chain termination procedure as described in Sanger et al., *Proc. Natl. Acad. Sci. U.S.A.* 74:5463–5467 (1977), which is incorporated herein by reference, to exclude the possibility of secondary mutations. The Hind III/BamH1 fragment was used together with a 3.2 kb BamH1/SmaI fragment of the b.IAP gene for directional subcloning into a Hind III/EcoRV opened pcDNA 1 expression vector (Invitrogen, San Diego, Calif.).

EXAMPLE V

Recombinant Expression of b.IAP

The b.IAP gene subcloned into pcDNA 1 was transfected into Chinese hamster ovary (CHO) cells, ATCC No. CCL61, by means of $Ca^{2+}$ coprecipitation as described in Hummer and Millan, *Biochem. J.* 274:91–95 (1991), which is incorporated herein by reference. The recombinant protein was extracted with butanol after incubating for 2 days.

The b.IAP gene presented in FIG. 1 includes an open reading frame (ORF) of 2946 bp, containing 11 exons and 10 introns of very compact nature. Exon and intron borders were determined by comparison with BB204 and other known AP genes described in Manes et al., supra, Hernthorn et al., *J. Biol. Chem.* 263:12011–12019 (1988), Knoll et al., *J. Biol. Chem.* 263:12020–12027 (1988), and Millan & Manes, *Proc. Natl. Acad. Sci. USA* 85:3025–3028 (1988). A translation initiation codon ATG was identified by sequence comparison to known TSAP genes and is preceded by an in-frame STOP codon 48 bp upstream. The ORF, which is terminated by the STOP codon TAA, codes for a peptide of 533 amino acids in length. The mature protein of 514 amino acids with a calculated $M_r$ of 64,400 Da is preceded by a hydrophobic signal peptide as is the case for all known APs.

Figure 3A:
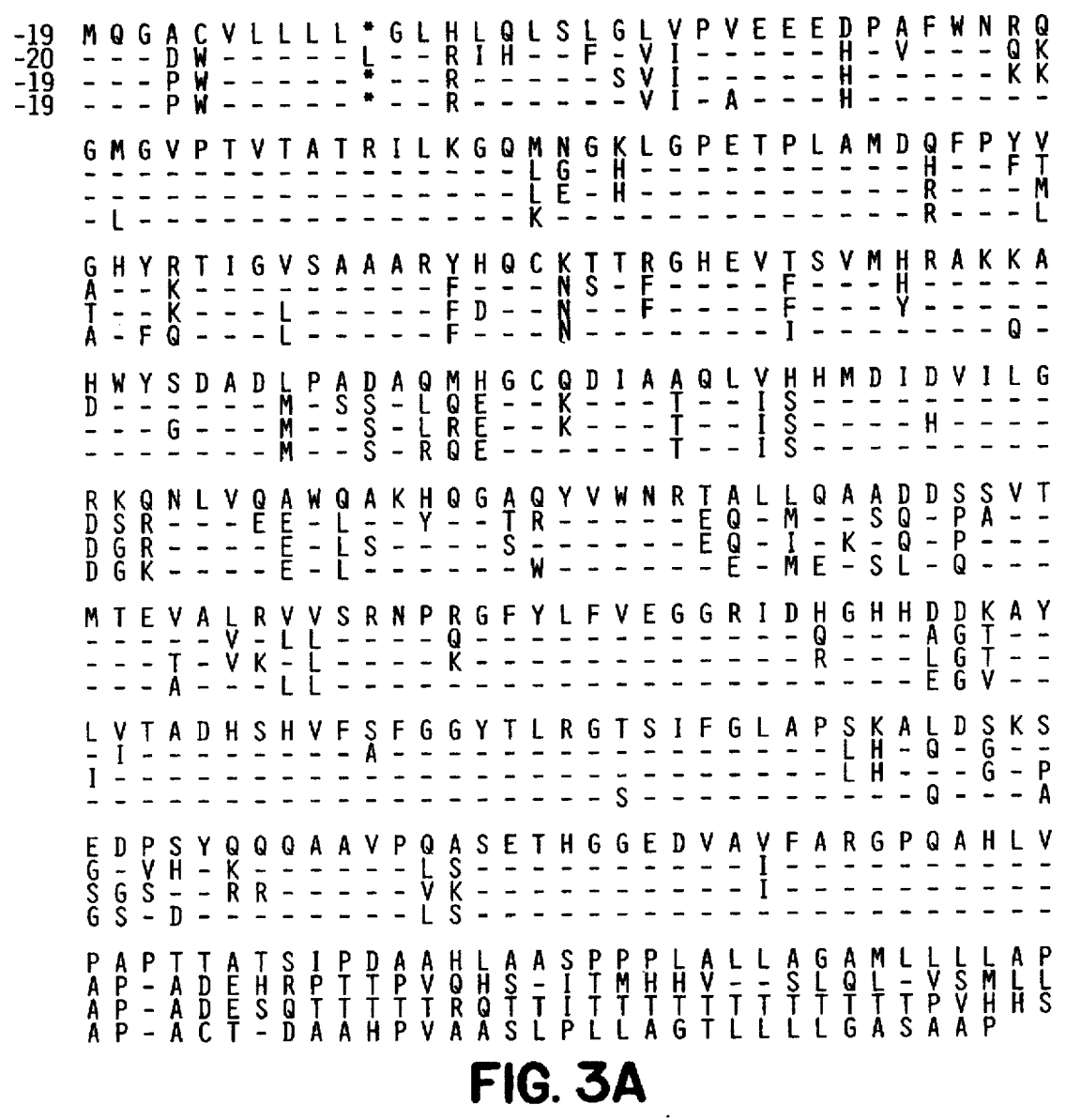

The predicted amino acid sequence of the b.IAP protein is highly homologous to other known IAPs as shown in FIG. 3. As shown in FIG. 3 there is identity in those parts corresponding to the partial amino acid sequences previously determined for b.IAP (Culp et al., supra; Besman and Coleman, supra). Besman & Coleman determined N-terminal amino acid sequences for two differentially expressed AP isozymes. The 16 N-terminal amino acids determined for the isozyme found only in newborn calves differ in three or four residues from the N-terminus of the enzyme exclusively expressed in adults.

EXAMPLE VI

Reverse Transcriptase-PCR

In order to construct a full length cDNA, reverse transcriptase-PCR (RT-PCR) was performed as follows: total RNA from a stable transfected CHO-cell clone (M2) was isolated by acid guanidium thiocyanate-phenol-chloroform extraction as described in Chomozynski & Sacchi, *Anal. Biochem.* 162:156–159 (1987), incorporated herein by reference. The reverse transcriptase reaction was conducted according to the protocol of the manufacturer (Promega, Wisconsin) using 10 µg of RNA.

The reaction mixture was extracted with phenol-chloroform, precipitated with ethanol and resuspended in Taq polymerase buffer. The subsequent PCR was performed over 35 cycles of amplification following an initial denaturation at 94° C. for 5 minutes, annealing at 55° C. for 30 seconds and extension at 72° C. for 5 minutes. The Taq Polymerase was added to the reaction mixture after denaturation only. The subsequent PCR settings were: denaturation at 94° C. for 45 seconds, annealing at 55° C. for 1 minute and extension at 72° C. for 4 minutes. The primers used for this reaction were MKNHE (SEQ ID NO: 1) and sequencing primer UP6: TCGGCCGCCTGAAGGAGC (SEQ ID NO: 3) (see FIG. 2).

The sequencing strategy as well as a restriction map and the genomic structure of the b.IAP gene are shown in FIG.

2. The strategies for subcloning the coding region of the gene into an expression vector using PCR and for construction of a full length cDNA by means of RT-PCR are indicated in FIG. 2. A single fragment of approximately 830 bp length had been obtained from RT-PCR as could be expected from the genomic sequence.

EXAMPLE VIII

Characterization of Recombinant Calf IAP

The sequence for the calf intestinal AP gene was determined as described above. A full length cDNA was constructed using a partial cDNA clone (BB204) and a fragment obtained by RT-PCR.

A cDNA fragment clone (R201) and a corresponding genomic clone were obtained, which resemble properties of a putative pseudogene. Both clones contain STOP codons within the coding region and several frameshifts. Bands corresponding to the putative pseudogene could only be identified upon hybridizing with a mouse TNAP cDNA which gave a distinct pattern. This result suggests that the bands correspond to TSAP genes only, and that the pseudogene is more related to TNAP. In contrast, the murine pseudogene has been found to resemble more homology to the mouse EAP gene (Manes et al., supra).

The sequence and genomic structure of the b.IAP gene show high homology to all known TSAP genes. The smallest exon, exon VII, is only 73 bp long while the longest exon, exon XI, is approximately 1.1 kb long. The exact length of exon 11 cannot be determined since no cDNA with a poly-A tail had been isolated. The estimate given is based on the identification of a putative poly-adenylation site AATAAA (bp 5183–5188) in the 3' non-coding region of the gene (underlined in FIG. 1). The introns are among the smallest introns reported (Hawkins, Nucl. Acids Res. 16:9893–9908 (1988)) as was found in the case of other TSAP genes as well (Manes et al., supra; Hernthorn et al., supra; Knoll et al., supra; Millan and Manes, supra). The largest one, splitting exon V and exon VI, is only 257 bp long. All exon-intron junctions conform to the GT-AG rule (Breathnach et al., Proc. Natl. Acad. Sci. USA 75:4853–4857 (1978)) and also conform well to the consensus sequences (C/A) AG/GT(A/G)AGT (SEQ ID NO: 4) and $(T/C)_nN(C/T)AG/G$ (SEQ ID NO: 5) for donor and acceptor sites, respectively (Mount, Nucl. Acids Res. 10:459–473 (1982)).

Interestingly, the entire coding region of exon XI shows a high G/C content of over 60 to 80% compared to a rather equal ratio of G/C to A/T throughout the whole structural gene. Other regions of biased GC content were found at bp 270 to bp 490 with a high A/T content and in a region preceding the poly adenylation site, which again shows a high G/C content.

A putative TATA-box has been identified in the 1.5 kb of sequence preceding the coding region (bp 1395–1400, underlined in FIG. 1). It shows the same variant ATTTAA sequence embedded in a conserved region of 25 bp as was previously reported for the mouse TSAP genes (Manes et al., supra) and two human TSAP genes (Millan, Nucl. Acids Res. 15:10599 (1987); Millan and Manes, supra)).

The sequence GGGAGGG has been shown to be part of the putative mouse TSAP promoters (Manes et al., supra) as well as of two human TSAP promoters (Millan, (1987), supra; Millan and Manes, supra). This sequence is also present in the putative promoter region of the b.IAP gene.

The sequence CACCC or its complementary reverse is repeated 6 times in the region of bp 1182–1341, 24 times in the entire structural gene and 31 times throughout the whole sequence shown here. However, only one less conserved CACCC box (Myers et al., Science 232:613–618 (1986)) was identified.

Since it was shown for dog IAP that the enzyme can be induced by cortico steroid hormone (Sanecki et al., Am. J. Vet. Res. 51, 12:1964–1968 (1990)), hormone responsive elements in the genomic sequence of b.IAP were identified. Palindromic and direct repeats, known to be binding sites for dimeric nuclear factors as described in O'Malley, Mol. Endocrinol. 5:94–99 (1990), were identified in the 1.5 kb upstream of the initiation codon. A long, imperfect palindromic repeat ($CACACCTCCTGCCCAG-N_7-CTGGTGAGGAGCTGAG$ (SEQ ID NO: 6)) extends from bp 899 to bp 937. A direct repeat of the sequence GGGCAGG spaced by three nucleotides starts at bp 1311.

Several regions of high homology to mouse (Manes et al., supra) and human (Millan, (1987), supra) IAP genes have been identified in the putative promoter region. However, one stretch of 10 bp (AGCCACACCC) (SEQ ID NO: 7) was found to be identical with a sequence in the same region upstream of the TATA box of the human β-globin gene (Myers et al., supra).

Another region of interest precedes the putative poly adenylation site at bp 5016. The sequence ACAGAGAG-GAGA (SEQ ID NO: 8) is imperfectly repeated, spaced by an invertedrepeat overlapping the last adenine nucleotide (ACAG-T-GACA). The presented 1.5 kb of the presumed promoter of the b.IAP gene contain several additional putative regulatory elements. A short stretch of 14 alternating thymines and quanines, intercepted by one adenine was found at position 601 of the sequence. Interestingly, this sequence is identical to a part of a slightly longer stretch with the same characteristics beginning at bp 2713 within the intron splitting exon V and VI. Another stretch of 36 alternating pyridines and purines is found at position 732 being mainly composed of cytosin and adenine nucleotides. Identical structures are reported for the human germ cell AP gene (Millan and Manes, supra) and are thought to form Z-DNA structures, which may play a role in the regulation of gene expression (Nordheim and Rich, Nature (London) 303:674–678 (1983)).

As shown in FIG. 3, the deduced amino acid sequence of b.IAP is highly homologous to all known IAPs. Identical residues and conservative amino acid substitutions are found within structurally important regions, as is the case for the other TSAPs as well, whereas variability is almost exclusively found at the C-terminus and in the highly variable loops (Millan, (1988), supra).

$Asp^{487}$ of b.IAP resides within a conserved sequence of 4 amino acids in the same region of the human intestinal gene (indicated in FIG. 3) as well as of human PLAP (Millan, J. Biol. Chem. 261:3112–3115 (1986)). This residue was shown for PLAP to be the attachment site of a phosphatidyl-inositol membrane anchor (Micanovic et al., Proc. Natl. Acad. Sci. USA 87:157–161 (1990)). Evidence has been presented previously that b.IAP is also anchored to the plasma membrane in such a fashion. There appears to be a spatial regulated release of IAP into the lumen without cleavage of the anchor in a variety of species (Hoffmann-Blume et al., Eur. J. Biochem. 199:305–312 (1991)).

EXAMPLE IX

Comparison of Purified and Recombinant Forms of Calf IAP

Values for $K_m$ and $K_L$ for L-Phe were determined for the recombinant enzyme as well as for purified protein from calf intestine as described in Hummer and Millan, supra, and Wilkinson, *Biochem. J.* 8:324–332 (1961), incorporated hereinby reference. Both the purified b.IAP from natural sources and the recombinant b.IAP show identical values for $K_m$ (within standard deviations), and only slightly different values of $K_L$. $K_m$ was determined as 0.77=0.12 for the recombinant enzyme and as 0.86±0.17 for the purified natural enzyme. $K_L$ for L-Phe were found to be 15.2±1.8 and 11.2±1.0 for the recombinant and purified enzymes, respectively. Thus, the results of these findings indicate that the natural and recombinant forms of calf IAP have comparable properties and activities.

Two possible glycosylation sites appear to be conserved between the human and the bovine IAP. Three other possible sites within other IAP sequences were not found in the b.IAP. The high degree of heterologous glycosylation of the purified enzyme was demonstrated by isoelectric focusing (IEF). IEF was performed using the Resolve-ALP system (Isolab, Akron, Ohio) as described in Griffiths & Black, *Clinn. Chem*, 33:2171–2177 (1987). Samples of recombinant and purified enzyme were run either treated with neuraminidase or untreated to compare the amount of glycosylation.

A smeary band was obtained upon IEF of untreated purified enzyme in contrast to a more distinct band for the recombinant b.IAP protein. After treatment with neuraminidase, both bands dissolve into several sharp bands, in which the purified enzyme showed considerably more diversity than the recombinant enzyme.

EXAMPLE X

Heat Inactivation of Calf IAP

Figure 4:
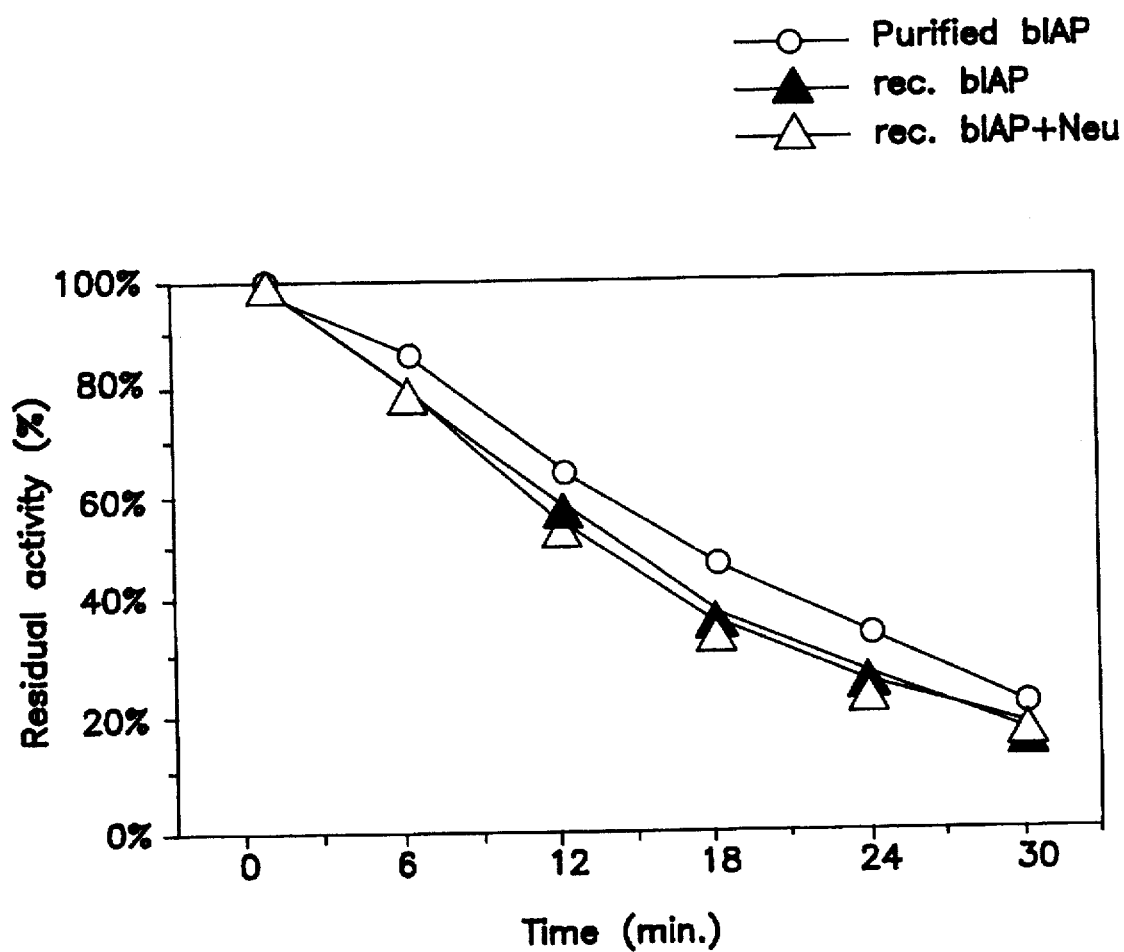
FIG. 4 shows the results of studies relating to the heat inactivation of purified and recombinant calf IAP.

The heat stabilities of purified calf IAP and recombinant calf IAP were determined at 56° C. First, the enzyme samples were diluted in 1 ml of DEA buffer containing 1M DEA diethanolamine (pH 9.8) containing 0.5 mM $MgCl_2$ and 20 µM $ZnCl_2$. The solution was heated at 56° C. for the fixed time intervals indicated in Table I. Fifty µl of the enzyme solution were removed and pipetted into a microtiter well and stored on ice until the end of the longest incubation period. At the end of the experiment, the residual activity was measured by the addition of 200 µl of DEA buffer containing p-nitrophenylphosphate (10 mM) in DEA buffer. For comparison, a sample of recombinant enzyme was pretreated with 0.2 units/ml of neuriminidase for 16 hours at room temperature, followed by the same heat inactivation treatment. The results of the heat inactivation studies are shown in FIG. 4.

TABLE I

Heat Inactivation of Intestinal AP

| | \multicolumn{6}{c}{Time (minutes)} | | | | | |
|---|---|---|---|---|---|---|
| | 0' | 6' | 12' | 18' | 24' | 30' |
| | | | Residual activity (%) | | | |
| Calf IAP (intestinal extract) | 100 | 87 | 65.6 | 48.7 | 36 | 23.4 |
| Recombinant IAP | 100 | 80.6 | 59.5 | 39.6 | 28.5 | 18.5 |
| Recombinant IAP upon Neuriminidase | 100 | 80.8 | 55.9 | 38.1 | 27.1 | 20.3 |

The foregoing description of the invention is exemplary for purposes of illustration and explanation. It should be understood that various modifications can be made without departing from the spirit and scope of the invention. Accordingly, the following claims are intended to be interpreted to embrace all such modifications.

---

I claim:

1. An isolated nucleic acid having a nucleotide sequence as shown in FIG. 1 (SEQ ID NO: 9).

2. A cDNA encoded by the nucleic acid molecule of claim 1.

3. An RNA encoded by the nucleic acid molecule of claim 1.

4. The isolated nucleic acid of claim 1, further comprising a second nucleotide sequence encoding a polypeptide having specific reactivity with a ligand.

5. A vector comprising the nucleic acid of claim 1.

6. The vector of claim 5, wherein said vector is a plasmid.

7. A recombinant host cell comprising the vector of claim 5.

8. A method of obtaining recombinant calf intestinal alkaline phosphatase comprising culturing said recombinant host cell of claim 7 and isolating said calf intestinal alkaline phosphatase from said culture.

9. A cell culture comprising the recombinant host cell of claim 7 cultured in a suitable medium.

* * * * *

UNITED STATES PATENT AND TRADEMARK OFFICE
CERTIFICATE OF CORRECTION

PATENT NO. : 5,707,853
DATED : January 13, 1998
INVENTOR(S) : Jose L. Millan

It is certified that error appears in the above-identified patent and that said Letters Patent is hereby corrected as shown below:

Column 5,
Line 11, please delete "also used." and replace therefor with -- also be used. --.

Column 10,
Line 61, please delete "*Blochem.*" and replace therefor with -- *Biochem.* --.
Line 66, please delete "and $K_L$" and replace therefor with -- and $K_i$ --.

Column 11,
Line 6, please delete "of $K_L$." and replace therefor with -- of $K_i$. --.
Line 8, please delete "$K_L$" and replace therefor with -- $K_i$ --.
Line 20, please delete "*Clinn. Chem,*" and replace therefor with -- *Clin. Chem.,* --.

Signed and Sealed this

Sixteenth Day of October, 2001

Attest:

NICHOLAS P. GODICI
Attesting Officer    Acting Director of the United States Patent and Trademark Office